US010316078B2

(12) United States Patent
Wang et al.

(10) Patent No.: US 10,316,078 B2
(45) Date of Patent: Jun. 11, 2019

(54) SEROTYPE CROSS-REACTIVE, DENGUE NEUTRALIZING ANTIBODY AND USES THEREOF

(71) Applicants: AGENCY FOR SCIENCE, TECHNOLOGY AND RESEARCH, Singapore (SG); National University of Singapore, Singapore (SG)

(72) Inventors: Cheng-I Wang, Singapore (SG); Katja Fink, Singapore (SG); Paul Macary, Singapore (SG); Roland Zuest, Singapore (SG); Meihui Xu, Singapore (SG)

(73) Assignees: AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/558,937

(22) PCT Filed: Mar. 17, 2016

(86) PCT No.: PCT/SG2016/050124
§ 371 (c)(1),
(2) Date: Sep. 15, 2017

(87) PCT Pub. No.: WO2016/148653
PCT Pub. Date: Sep. 22, 2016

(65) Prior Publication Data

US 2018/0072798 A1 Mar. 15, 2018

(30) Foreign Application Priority Data

Mar. 17, 2015 (SG) .......................... 10201502068V

(51) Int. Cl.

| | |
|---|---|
| ***C07K 16/10*** | (2006.01) |
| ***G01N 33/569*** | (2006.01) |
| ***A61P 31/12*** | (2006.01) |
| *A61K 39/00* | (2006.01) |

(52) U.S. Cl.
CPC .......... *C07K 16/1081* (2013.01); *A61P 31/12* (2018.01); *G01N 33/56983* (2013.01); *A61K 2039/505* (2013.01); *C07K 2317/34* (2013.01); *C07K 2317/76* (2013.01); *G01N 2333/185* (2013.01); *Y02A 50/386* (2018.01); *Y02A 50/53* (2018.01)

(58) Field of Classification Search
None
See application file for complete search history.

(56) References Cited

U.S. PATENT DOCUMENTS

| | | | |
|---|---|---|---|
| 6,753,418 | B2 | 6/2004 | Montano et al. |
| 8,470,976 | B2 | 6/2013 | Chook |

FOREIGN PATENT DOCUMENTS

| | | | |
|---|---|---|---|
| WO | WO 2010/043977 | A2 | 4/2010 |
| WO | WO 2012/130831 | A1 | 10/2012 |
| WO | WO 2013/089647 | A1 | 6/2013 |
| WO | WO 2013/173348 | A1 | 11/2013 |

OTHER PUBLICATIONS

Rudikoff et al. Single amino acid substitution altering antigen-binding specificity. Proc. Natl. Acad. Sci. U.S.A., 1982, 79:1979-1983.*
PCT International Search Report for PCT Counterpart Application No. PCT/SG2016/050124, 6 pgs. (dated May 10, 2016).
PCT Written Opinion for PCT Counterpart Application No. PCT/SG2016/050124, 5 pgs. (dated May 10, 2016).
MeiHui Xu, et al., "Plasmablasts Generated during Repeated Dengue Infection Are Virus Glycoprotein-Specific and Bind to Multiple Virus Serotypes," J Immunol, vol. 189, No. 12, pp. 5877-5885 (Nov. 14, 2012).
Ruklanthi de Alwis, et al., "Identification of human neutralizing antibodies that bind to complex epitopes on dengue virions," Proc Natl Acad Sci USA, vol. 109, No. 19, pp. 7439-7444 (Apr. 12, 2012).
Wen-Yang Tsai, et al., "High-Avidity and Potently Neutralizing Cross-Reactive Human Monoclonal Antibodies Derived from Secondary Dengue Virus Infection," J Virol, vol. 87, No. 23, pp. 12562-12575 (Sep. 11, 2013).
Martina Beltramello, et al., "The Human Immune Response to Dengue Virus Is Dominated by Highly Cross-Reactive Antibodies Endowed with Neutralizing and Enhancing Activity," Cell Host Microbe, vol. 8. No. 3, pp. 271-283 (Sep. 15, 2010).
Kenneth Smith, et al., "Rapid generation of fully human monoclonal antibodies specific to a vaccinating antigen," Nature Protocols, vol. 4, No. 3, pp. 372-384 (2009).
M. Umashankar, et al., "Differential Cholesterol Binding by Class II Fusion Proteins Determines Membrane Fusion Properties," Journal of Virology, vol. 82, No. 18, p. 9245-9253 (Sep. 2008).
Wayne D. Crill et al., "Monoclonal Antibodies That Bind to Domain III of Dengue Virus E Glycoprotein Are the Most Efficient Blocker of Virus Adsorption to Vero Cells," Journal of Virology, vol. 75, No. 16, pp. 7769-7773 (Aug. 2001).
Ravijumar Rajamanonmani, et al., "On a mouse monoclonal antibody that neutralizes all four dengue virus serotypes," Journal of General Virology, vol. 90, pp. 799-809 (Apr. 1, 2009).

(Continued)

*Primary Examiner* — Nianxiang Zou
(74) *Attorney, Agent, or Firm* — Womble Bond Dickinson (US) LLP

(57) ABSTRACT

Disclosed are isolated antibodies, or antigen binding fragments thereof, that bind to dengue virus epitopes, as well as kits containing them, compositions containing them, and passive vaccines comprising them, in one embodiment, the antibody or antigen binding fragment thereof is capable of binding to a whole dengue virus particle better than binding to a dengue virus surface glycoprotein. Also disclosed are methods of using the antibodies or antigen binding fragments thereof, nucleic acids encoding them, vectors expressing the nucleic acids, host producing them, and methods of manufacturing them.

16 Claims, 17 Drawing Sheets

Specification includes a Sequence Listing.

(56) References Cited

OTHER PUBLICATIONS

Matthew R. Vogt, et al., "Human Monoclonal Antibodies against West Nile Virus Induced by Natural Infection Neutralize at a Postattachment Step," Journal of Virology, vol. 83, No. 13, pp. 6494-6507 (Jul. 2009).
Extended European Search Report for counterpart EP Application No. 16765356.7, 10 pgs. (dated Jul. 6, 2018).
Xu Meihui, et al., "A potent neutralizing antibody with therapeutic potential against all four serotypes of dengue virus," XP055487231, NPJ Vaccines, vol. 2, No. 1, p. 10 (Jan. 23, 2017).
Luke N. Robinson, et al., "Structure-Guided Design of an Anti-dengue Antibody Directed to a Non-immunodominant Epitope," XP029248088, Cell, vol. 162, No. 3, pp. 493-504 (Jul. 16, 2015).
Scott A. Smith, et al., "The Potent and Broadly Neutralizing Human Dengue Virus-Specific Monclonal Antibody 1C19 Reveals a Unique Cross-Reactive Epitope on the bc Loop of Domain II of the Envelope Protein," XP055487227, MBIO, vol. 4, No. 6, 12 pgs. (Nov. 19, 2013).
Wanwisa Dejniraltisai, et al., "A new class of highly potent, broadly neutralizing antibodies isloated from viremic patients infected with dengue virus," XP055230957, Nature Immunology, vol. 16, No. 2, pp. 170-177 (Feb. 2015).

* cited by examiner

| | DENV1 | DENV2 | DENV3 | DENV4 |
|---|---|---|---|---|
| EC50 | 0.05955 | 0.001028 | 0.4657 | 0.07496 |

A)

B)

A)

B)

A)

B)

A)

B)

A)

B)

A)

B)

A)

B)

Sequence for Ab 3C-H5L1

Heavy Chain variable region nucleotide sequence (SEQ ID NO: 1):

> He_3C5

GAGGTCCAGCTGGTACAGTCTGGGCCTGACGTCGAGAAGCCTGGGGCCTCAGTGAAGGTTTC
CTGCAAGGCATCTGGATACACCTTCACCAGCAACTATATACACTGGGTGCGACAGGCCCCTG
GACAAGGGCTTGAGTGGATGGGGGTAATCAACCCTAGGGGTGGTAGCACAGCCAGCGCACAG
AAATTCCAGGGAAGAATCACCATGACCAGGGACACGTCCACGAGCACAGTTTACATGGAACT
GAGCAGCCTGAGATCTGACGACACGGCCGTGTATTACTGTGCGAGAGGGGGAAGGGCCCTTT
TCTATGATAGTTACACGACCCCCCGAGACGGAGGGTCGTGGTGGTTCGACCCCTGGGGCCAG
GGAAGCCTGGTCACCGTCTCCTCA

Heavy chain variable region Amino Acid Sequence (SEQ ID NO: 9):

> He_3C5

EVQLVQSGPDVEKPGASVKVSCKASGYTFTSNYIHWVRQAPGQGLEWMGVINPRGGSTASAQ
KFQGRITMTRDTSTSTVYMELSSLRSDDTAVYYCARGGRALFYDSYTTPRDGGSWWFDPWGQ
GSLVTVSS

CDR Analysis (He_3C5)
(SEQ ID NO: 3) (SEQ ID NO: 4) (SEQ ID NO: 5)

----CDRH1---> <--CDRH2--> <---CDRH3----
GYTFTSNY....___INPRGGST..___ARGGRALFYDSYTTPRDGGSWWFDP

Light chain variable region nucleotide sequence(SEQ ID NO: 2):

> Li_3C1

GACATCCAGTTGACCCAGTCTCCATCTTCCCTGTCTGCATCTGTAGGAGACAGAGTCACCTT
CACTTGCCAGGCGAGCCAGGACATTAGGAAGTATTTAAATTGGTATCAGCAGAAACCAGGGA
AAGCCCCTAAACTCCTAATCTACGATGCATCCAATTTGAAAACAGGGGTCCCATCAAGGTTC
AGTGGAAGTGGATCTGGGACAGATTTTACTTTCACCATCAGCAGCCTGCAGCCTGAAGATGT
TGCAACATACTACTGTCAACAGTTTGATGATCTCCCGATCACCTTCGGCCAGGGGACACGAC
TGCAGATTAAACGA

Light chain variable region Amino Acid Sequence(SEQ ID NO: 10):

> Li_3C1

DIQLTQSPSSLSASVGDRVTFTCQASQDIRKYLNWYQQKPGKAPKLLIYDASNLKTGVPSRF
SGSGSGTDFTFTISSLQPEDVATYYCQQFDDLPITFGQGTRLQIK

CDR Analysis (Li_3C1)
(SEQ ID NO: 6) (SEQ ID NO: 7) (SEQ ID NO: 8)

----CDRL1---> <--CDRL2--> <---CDRL3----
QDIRKY......______DAS.......___QQFDDLPIT

Fig. 21

3C H5L1 heavy chain constant region with LALA mutation (nucleotide sequence)

GCTTCCACCAAGGGCCCATCGGTCTTCCCCCTGGCACCCTCCTCCAAGTCGACCTCT
GGGGGCACAGCGGCCCTGGGCTGCCTGGTCAAGGACTACTTCCCCGAACCGGTGACG
GTGTCGTGGAACTCAGGCGCCCTGACCAGTGGCGTGCACACCTTCCCGGCTGTCCTA
CAGTCCTCAGGACTCTACTCCCTCAGTAGTGTGGTGACCGTGCCCTCCAGTAGTTTG
GGCACCCAGACCTACATCTGCAACGTGAATCACAAGCCCAGTAACACCAAGGTGGAC
AAGAGAGTTGAGCCCAAATCTTGTGACAAAACTCACACATGCCCACCGTGCCCAGCA
CCTGAGGCCGCCGGGGGACCGTCAGTCTTCCTCTTCCCCCCAAAACCCAAGGACACC
CTCATGATCTCCCGGACCCCTGAGGTCACATGCGTGGTGGTGGACGTGAGTCACGAA
GACCCTGAGGTCAAGTTCAACTGGTACGTGGACGGCGTGGAGGTGCATAATGCCAAG
ACAAAGCCGCGGGAGGAGCAGTACAACAGTACGTACCGTGTGGTCAGTGTCCTCACC
GTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAA
CCACAGGTGTACACCCTGCCCCCATCCCGGGAGGAGATGACCAAGAACCAGGTCAGT
CTGACCTGCCTGGTCAAAGGCTTCTATCCCAGTGACATCGCCGTGGAGTGGGAGAGT
AATGGGCAGCCGGAGAACAACTACAAGACCACGCCTCCCGTGCTGGACTCCGACGGC
TCCTTCTTCCTCTACAGTAAGCTCACCGTGGACAAGAGTAGGTGGCAGCAGGGGAAC
GTCTTCTCATGCTCCGTGATGCATGAGGCTCTGCACAACCACTACACGCAGAAGAGT
CTCTCCCTGTCTCCG (SEQ ID NO: 11)

3C H5L1 heavy chain constant region with LALA mutation (amino acid sequence)

ASTKGPSVFPLAPSSKSTSGGTAALGCLVKDYFPEPVTVSWNS*GALT*SGVHTFPAVL
QSSGLYSLSSVVTVPSSSLGTQTYICNVNHKPSNTKVDKRVEPKSCDKTHTCPPCPA
PEAAGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSP (SEQ ID NO: 12)

Fig.22

SEQUENCE LISTING

```
<160> NUMBER OF SEQ ID NOS: 12

<210> SEQ ID NO 1
<211> LENGTH: 396
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<223> OTHER INFORMATION: Heavy chain variable region

<400> SEQUENCE: 1

gaggtccagc tggtacagtc tgggcctgac gtcgagaagc ctggggcctc agtgaaggtt     60

tcctgcaagg catctggata caccttcacc agcaactata tacactgggt gcgacaggcc    120

cctggacaag ggcttgagtg gatgggggta atcaacccta ggggtggtag cacagccagc    180

gcacagaaat tccagggaag aatcaccatg accagggaca cgtccacgag cacagtttac    240

atggaactga gcagcctgag atctgacgac acggccgtgt attactgtgc gagaggggga    300

agggcccttt tctatgatag ttacacgacc ccccgagacg gagggtcgtg gtggttcgac    360

ccctggggcc agggaagcct ggtcaccgtc tcctca                              396


<210> SEQ ID NO 2
<211> LENGTH: 324
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<223> OTHER INFORMATION: Light chain variable region

<400> SEQUENCE: 2

gacatccagt tgacccagtc tccatcttcc ctgtctgcat ctgtaggaga cagagtcacc     60

ttcacttgcc aggcgagcca ggacattagg aagtatttaa attggtatca gcagaaacca    120

gggaaagccc ctaaactcct aatctacgat gcatccaatt tgaaaacagg ggtcccatca    180

aggttcagtg gaagtggatc tgggacagat tttactttca ccatcagcag cctgcagcct    240

gaagatgttg caacatacta ctgtcaacag tttgatgatc tcccgatcac cttcggccag    300

gggacacgac tgcagattaa acga                                           324


<210> SEQ ID NO 3
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: CDRH1

<400> SEQUENCE: 3

Gly Tyr Thr Phe Thr Ser Asn Tyr
1               5
```

-continued

<210> SEQ ID NO 4
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: CDRH2

<400> SEQUENCE: 4

Ile Asn Pro Arg Gly Gly Ser Thr
1               5

<210> SEQ ID NO 5
<211> LENGTH: 25
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: CDRH3

<400> SEQUENCE: 5

Ala Arg Gly Gly Arg Ala Leu Phe Tyr Asp Ser Tyr Thr Thr Pro Arg
1               5                   10                  15

Asp Gly Gly Ser Trp Trp Phe Asp Pro
            20                  25

<210> SEQ ID NO 6
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: CDRL1

<400> SEQUENCE: 6

Gln Asp Ile Arg Lys Tyr
1               5

<210> SEQ ID NO 7
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: CDRL2
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

Asp Ala Ser Xaa
1

<210> SEQ ID NO 8
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE -continued

<223> OTHER INFORMATION: CDRL3

<400> SEQUENCE: 8

```
Gln Gln Phe Asp Asp Leu Pro Ile Thr
1               5
```

<210> SEQ ID NO 9
<211> LENGTH: 132
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: Heavy chain variable region

<400> SEQUENCE: 9

```
Glu Val Gln Leu Val Gln Ser Gly Pro Asp Val Glu Lys Pro Gly Ala
1               5                   10                  15

Ser Val Lys Val Ser Cys Lys Ala Ser Gly Tyr Thr Phe Thr Ser Asn
            20                  25                  30

Tyr Ile His Trp Val Arg Gln Ala Pro Gly Gln Gly Leu Glu Trp Met
        35                  40                  45

Gly Val Ile Asn Pro Arg Gly Gly Ser Thr Ala Ser Ala Gln Lys Phe
    50                  55                  60

Gln Gly Arg Ile Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Gly Gly Arg Ala Leu Phe Tyr Asp Ser Tyr Thr Thr Pro Arg
            100                 105                 110

Asp Gly Gly Ser Trp Trp Phe Asp Pro Trp Gly Gln Gly Ser Leu Val
        115                 120                 125

Thr Val Ser Ser
    130
```

<210> SEQ ID NO 10
<211> LENGTH: 107
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: Light chain variable region

<400> SEQUENCE: 10

```
Asp Ile Gln Leu Thr Gln Ser Pro Ser Ser Leu Ser Ala Ser Val Gly
1               5                   10                  15

Asp Arg Val Thr Phe Thr Cys Gln Ala Ser Gln Asp Ile Arg Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Lys Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Tyr Cys Gln Gln Phe Asp Asp Leu Pro Ile
                85                  90                  95

Thr Phe Gly Gln Gly Thr Arg Leu Gln Ile Lys
```

-continued 100 105

<210> SEQ ID NO 11
<211> LENGTH: 984
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<223> OTHER INFORMATION: 3C H5L1 heavy chain constant region with LALA mutation

<400> SEQUENCE: 11

```
gcttccacca agggcccatc ggtcttcccc ctggcaccct cctccaagtc gacctctggg     60

ggcacagcgg ccctgggctg cctggtcaag gactacttcc ccgaaccggt gacggtgtcg    120

tggaactcag gcgccctgac cagtggcgtg cacaccttcc cggctgtcct acagtcctca    180

ggactctact ccctcagtag tgtggtgacc gtgccctcca gtagtttggg cacccagacc    240

tacatctgca acgtgaatca caagcccagt aacaccaagg tggacaagag agttgagccc    300

aaatcttgtg acaaaactca cacatgccca ccgtgcccag cacctgaggc cgccgggggga    360

ccgtcagtct tcctcttccc cccaaaaccc aaggacaccc tcatgatctc ccggacccct    420

gaggtcacat gcgtggtggt ggacgtgagt cacgaagacc ctgaggtcaa gttcaactgg    480

tacgtggacg gcgtggaggt gcataatgcc aagacaaagc cgcgggagga gcagtacaac    540

agtacgtacc gtgtggtcag tgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag tctgacctgc ctggtcaaag gcttctatcc cagtgacatc    780

gccgtggagt gggagagtaa tgggcagccg gagaacaact acaagaccac gcctcccgtg    840

ctggactccg acggctcctt cttcctctac agtaagctca ccgtggacaa gagtaggtgg    900

cagcagggga acgtcttctc atgctccgtg atgcatgagg ctctgcacaa ccactacacg    960

cagaagagtc tctccctgtc tccg                                           984
```

<210> SEQ ID NO 12
<211> LENGTH: 328
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<223> OTHER INFORMATION: 3C H5L1 heavy chain constant region with LALA mutation
<220> FEATURE:
<221> NAME/KEY: MISC_FEATURE
<222> LOCATION: (117)..(118)
<223> OTHER INFORMATION: LALA mutation

<400> SEQUENCE: 12

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

SEROTYPE CROSS-REACTIVE, DENGUE NEUTRALIZING ANTIBODY AND USES THEREOF

CROSS-REFERENCE TO RELATED APPLICATIONS

This patent application is a U.S. National Phase Application under 35 U.S.C. § 371 of International Application No. PCT/SG2016/050124, filed on 17 Mar. 2016, entitled A SEROTYPE CROSS-REACTIVE, DENGUE NEUTRALIZING ANTIBODY AND USES THEREOF, which claims priority to Singapore patent application No, 10201502068V filed on 17 Mar. 2015, the contents of which were incorporated by reference in their entirety for all purposes.

INCORPORATION BY REFERENCE

This patent application incorporates by reference the material (i.e., Sequence Listing) in the ASCII text file named Sequence_Listing_3503780_1.txt, created on Sep. 8, 2017, having a file size of 12,288 bytes.

FIELD OF THE INVENTION

The present invention relates to a preparation for medical purpose or specific therapeutic activity of a preparation. In particular, the present invention relates to antibodies and other agents that bind to dengue virus (or DENV), as well as to methods of using the antibodies or other agents for the treatment of diseases.

BACKGROUND OF THE INVENTION

Dengue fever is the most common arthropod-borne viral disease in the world. The virus causing dengue (i.e. DENV) can be divided into four different infective serotypes such as DENV-1, DENV-2, DENV-3, and DENV-4. Symptoms of dengue infection include fever, muscle pain, headache, low platelet numbers and low white blood cell numbers, coagulopathy, bleeding and vascular leakage that can lead to dengue shock syndrome. When a person is exposed to the dengue virus after a previous dengue infection, antiviral antibodies may enhance the uptake of virus into host cells and the patient is at higher risk to develop a severe form or dengue. Severe forms of dengue can, however, also occur during a first infection.

Whilst being the most common arthropod-borne viral disease, to date, there is no drug for dengue. Approaches with regards to dengue have mainly been towards the prevention of the infection and/or treatment to alleviate symptoms.

Thus, there is a need to provide agents capable of neutralizing and/or binding to at least one dengue serotype.

SUMMARY OF THE INVENTION

In one aspect there is provided an isolated antibody, or antigen binding fragment thereof, wherein the antibody comprises at least: one heavy chain amino acid sequences comprising at least one CDR selected from the group consisting of (a) a CDRH1 as shown in SEQ ID NO: 3, or a CDRH1 sequence having at least 70% sequence identity to SEQ ID NO: 3 therefrom, (b) a CDRH2 as shown in SEQ ID NO: 4, or a CDRH2 sequence having at least 70% sequence identity to SEQ ID NO: 4 therefrom, (c) a CDRH3 as shown in SEQ ID NO: 5, or a CDRH3 sequence having at least 70% sequence identity to SEQ ID NO: 5 therefrom, or an antibody, or antigen binding fragment thereof.

In another aspect there is provided an isolated antibody, or antigen binding fragment thereof, wherein the antibody comprises at least: one light chain amino acid sequences comprising at least one CDR selected from the group consisting of: (a) a CDRL1 as shown in SEQ ID NO: 6, or a CDRL1 sequence having at least 70% sequence identity to SEQ ID NO: 6 therefrom, (b) a CDRL2 as shown in SEQ ID NO: 7, or a CDRL2 sequence having at least 70% sequence identity to SEQ ID NO: 7 therefrom, (c) a CDRL3 as shown in SEQ ID NO: 8, or a CDRL3 sequence having at least 70% to SEQ ID NO: 8 therefrom, or an antibody, or antigen binding fragment thereof.

In yet another aspect, there is provided an isolated antibody, or antigen binding fragment thereof, wherein the antibody comprises at least: one heavy chain amino acid sequences comprising at least one CDR selected from the group consisting of (a) a CDRH1 as shown in SEQ ID NO: 3, or a CDRH1 sequence differing 1 or 2 amino acids therefrom, (b) a CDRH2 as shown in SEQ ID NO: 4, or a CDRH2 sequence differing 1 or 2 amino acids therefrom, (c) a CDRH3 as shown in SEQ ID NO: 5, or a CDRH3 sequence differing 1 or 2 amino acids therefrom, and/or at least one light chain amino acid sequences comprising at least one CDR selected from the group consisting of (a) a CDRL1 as shown in SEQ ID NO: 6, or a CDRL1 sequence differing 1 or 2 amino acids therefrom, (b) a CDRL2 as shown in SEQ ID NO: 7, or a CDRL2 sequence differing 1 or 2 amino acids therefrom, (c) a CDRL3 as shown in SEQ ID NO: 8, or a CDRL3 sequence differing 1 or 2 amino acids therefrom, or an antibody, or antigen binding fragment thereof, recognizing a whole dengue virus particle.

In yet another aspect there is provided a composition comprising the isolated antibody, or antigen binding fragment thereof, as described herein.

In yet another aspect there is provided a kit comprising the isolated antibody as described herein.

In yet another aspect there is a passive vaccine against at least one of the dengue virus serotypes comprising the isolated antibody as described herein, or the composition as described herein, or the kit as described herein.

In yet another aspect there is provided a method of treating a dengue virus infection in a subject comprising administering to the subject an effective amount of the isolated antibody, or antigen binding fragment thereof, as described herein, or the composition as described herein, or the vaccine as described herein.

In yet another aspect there is provided a use of the antibody, or antigen binding fragment thereof, as described herein or the composition as described herein, or the kit as described herein, or the vaccine as described herein, in the manufacture of a medicament for treating a dengue virus infection in a subject.

In yet another aspect there is provided a method for detecting at least one dengue virus serotype in a sample. In one example, the method comprises: (a) incubating the sample with at least one of the isolated antibody as described herein, or kit as described herein, and (b) detecting the antibody-dengue virus complex wherein the presence or absence of the complex indicates the presence or absence of dengue virus in the sample.

In yet another aspect there is provide an isolated nucleic acid molecule selected from the group consisting of: (a) a nucleic acid sequence encoding the isolated antibody, or antibody fragment thereof, as described herein, (b) a nucleic acid sequence as shown in SEQ ID NOs: 1 and 2, (c) a nucleic acid complementary to any one of the sequences in (a) or (b); and (d) a nucleic acid sequence capable of hybridizing to (a), (b), or (c) under stringent conditions.

In yet another aspect there is provided a vector comprising a nucleic acid sequence as described herein.

In yet another aspect there is provided a host transformed with the vector as described herein.

In yet another aspect there is provided a process of manufacturing an antibody, or antigen binding fragment, as described herein, comprising the step of obtaining the antibody from the host as described herein.

BRIEF DESCRIPTION OF THE DRAWINGS

The invention will be better understood with reference to the detailed description when considered in conjunction with the non-limiting examples and the accompanying drawings, in which:

FIG. 1 shows the initial characterization of 3C-H5L1 antibody.

FIG. 2 shows that 3C H5L1 binds to all four serotypes of dengue virus when the virus is not inactivated.

FIG. 4 shows potent in vitro neutralization capacity against all four serotypes, wherein DENV2 was neutralized at $EC_{50}$ of 0.001 μg/ml, followed by DENV1, 4, and 3, which were neutralized at 0.6 μg/ml, 0.07 μg/ml, and 0.5 μg/ml, respectively. Thus, FIG. 4 shows 3C H5L1 antibody is capable of neutralizing all four serotypes of DENV.

FIG. 5 shows modified 3C H5L1 antibody could neutralize both DENV-1 and DENV-2 serotypes when presented before or after infection.

FIG. 7 shows both modified and wild type (i.e. 3C-LALA and 3C-WT, respectively) 3C antibody could significantly prevent fusion of DENV-2 into cells.

FIG. 8 shows modified 3C antibody can significantly prevent fusion of dengue virus.

FIG. 10 shows 3C H5L1 monoclonal antibody could protect mice from dengue virus infection caused by at least DENV-1, DENV-2 and DENV-3 serotypes.

FIG. 11 shows all mice receiving 3C H5L1 (with varying concentrations) survived the infection. In contrast, none of the mice receiving control antibodies survived the infection. Thus, FIG. 11 shows 3C antibody can protect mice from death caused by dengue virus infection.

FIG. 12 shows the validation of the efficacy of modified 3C antibody in preventing antibody-dependent enhancement (ADE) of dengue infection. K562 cells were infected in the presence of different amounts of 3C H5L1 in its unmodified form (i.e. IgG1) or in a mutated form to interfere with Fcgamma-Receptor binding (i.e. with LALA mutation). FIG. 12 shows ADE manifested in a spike in the pfu measured in cells treated with unmodified 3C H5L1 (in box). In contrast, cells treated with modified 3C H5L1 did not show a spike in the pfu measured. Thus, FIG. 12 shows introduction of LALA mutation into 3C H5L1 antibody abolishes ADE in vitro.

FIG. 13 shows both modified and unmodified 3C H5L1 antibodies protect mice in a dose dependent manner.

FIG. 14A) shows the virus titres in IFNAR mice infected with DENV1 and B) shows virus titres in IFNAR mice infected with DENV2. Viremia was tested at day 3 after infection. Thus, FIG. 14 shows mice treated with modified 3C H5L1 antibody has significantly lower serum virus titre as compared to mice treated with PBS control or 513 Visterra antibody (modified with LALA mutation). Thus, FIG. 14 shows modified 3C H5L1 antibody can decrease serum virus titre in mice better than control antibodies.

FIG. 15 A) shows the virus titres in AG129 mice infected with DENV3 and B) shows virus titres in AG129 mice infected with DENV4. Viremia was tested at day 4 after infection. FIG. 15 shows mice treated with modified 3C H5L1 antibody has lower serum virus titre as compared to mice treated with PBS control or 513 Visterra antibody (modified with LALA mutation). Thus, FIG. 15 shows modified 3C H5L1 antibody can decrease serum virus titre in mice better than control antibodies.

FIG. 16 B) shows the survival curve of AG129 mice treated with 3C H5L1 antibody or control antibodies. FIG. 16 shows 3C H5L1 can be used as a therapeutic antibody post dengue virus infection.

FIG. 17 shows mice receiving 3C antibodies either pre-infection or post-infection could survive the lethal challenge with dengue virus. Of note, AG129 mice treated therapeutically die between day 20 and 35 after infection (FIG. 16) whereas IFNAR mice survive until at least day 32 (FIG. 17B). This suggests that the lack of the interferon gamma receptor in AG129 mice combined with the lack of the interferon alpha/beta receptor makes them more susceptible to infection compared to IFNAR mice which only lack the interferon alpha/beta receptor.

FIG. 18 shows that at low doses, modified 3C H5L1 is at least as efficient as unmodified 3C H5L1 in reducing virus titre in AG129 mice.

FIG. 19 shows the LALA modification of 3C H5L1 does not change its efficacy in reducing virus titre in either AG129 or IFNAR mice.

In FIG. 20A, relative binding of 3C H5L1 to the E protein mutants are indicated on the x-axis. The binding to wildtype protein (wt E protein) was used to normalize binding to mutants. The binding observed using the HEK cell approach is indicated in grey bars whereas the binding observed in ELISA is indicated in black bars. For K64A, G100A, F108A, Q167A, S274A only ELISA was done. For K122A, I162A, Q200A, E202A, K310A, W391A and F392A only the HEK cell expression assay was done. The dotted line indicates 75% reduction in binding compared to wt E protein that was arbitrarily chosen as a cut-off for loss of binding due to the mutation. In FIG. 20 B) the residues identified in the epitope mapping assays are illustrated on a publicly available E protein dimer structure (PDB accession number 1OAN). The eight amino acids identified (see Table 1) are highlighted with white dots in one E protein monomer (upper, lighter grey protein) and with grey dots in the second E protein monomer (lower, darker grey protein). Note that residue F392 for the second E protein monomer is hidden in the illustration, and hence the grey dots do not add up to eight.

FIG. 21 shows the nucleotide and amino acid sequences of the antibody 3C H5L1.

FIG. 22 shows the nucleotide and amino acid sequence of the antibody 3C H5L1 heavy chain with LALA mutation. The mutation is indicated in bold characters in the amino acid sequence.

DETAILED DESCRIPTION OF THE PRESENT INVENTION

Figure 1:
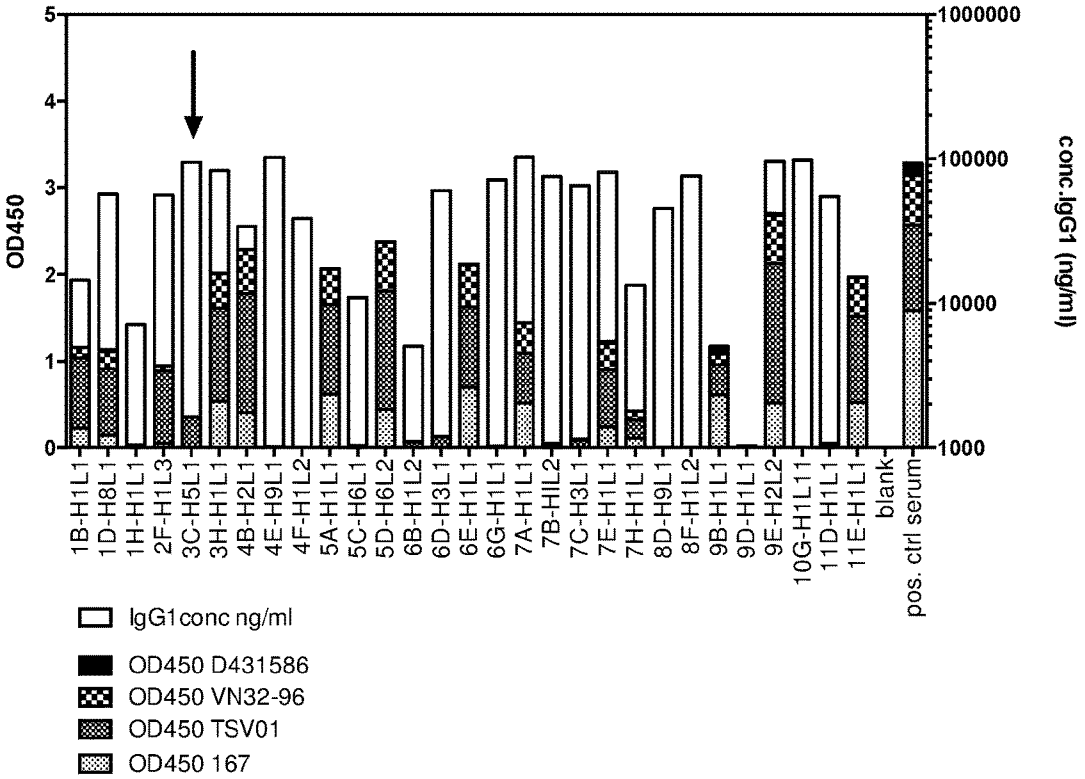
FIG. 1 shows a bar graph of the initial screening of mAbs on UV-inactivated DENV-1, DENV-2, DENV-3, and DENV-4. The 3C-H5L1 antibody clone (pointed with an arrow) showed low binding to inactivated dengue virus particles, regardless of the serotype (bottom bar adjacent to x-axis). The expression level of 3C-H5L1 antibody was high (grey bar-top bar) as seen in the total concentration of IgG1 in ng/ml (right y-axis). Thus.

Dengue virus is a common health problem in the tropical and subtropical regions of the world. Dengue virus (or referred to herein as "DENV") is a positive sense single stranded RNA virus of approximately 11 kb genome of the genus *Flavivirus*, family Flaviviridae. Flaviviruses encode a single polyprotein that is processed by host and viral proteases to produce three structural proteins, i.e. capsid (C) protein, precursor membrane/membrane (prM/M) and envelope (E) protein, and seven nonstructural proteins (NS1, NS2A, NS2B, NS3, NS4A, NS4B, and NS5). Antibodies play an important role in protection against DENV.

In the present disclosure, the inventors of the present invention found an alternative antibody (to those known in the art) that is capable of binding DENV. Thus, in one aspect, there is provided an isolated antibody, or antigen binding fragment thereof. In one example, the antibody comprises at least: one heavy chain amino acid sequences comprising at least one CDR selected from the group consisting of (a) a CDRH1 as shown in SEQ ID NO: 3, or a CDRH1 sequence having at least 70% sequence identity to SEQ ID NO: 3 therefrom, (b) a CDRH2 as shown in SEQ ID NO: 4, or a CDRH2 sequence having at least 70% sequence identity to SEQ ID NO: 4 therefrom, (c) a CDRH3 as shown in SEQ ID NO: 5, or a CDRH3 sequence having at least 70% sequence identity to SEQ ID NO: 5 therefrom, or an antibody, or antigen binding fragment thereof.

As used herein, the term "antibody", which may be used interchangeably with "antibodies", refers to the usual term known in the art, which refers to an immunoglobulin that binds specifically to a particular antigen. The term encompasses immunoglobulins that are naturally produced in that they are generated by an organism reacting to the antigen, and also those that are synthetically produced or engineered. In one example, the antibody may be a monoclonal antibody or polyclonal antibody. In one example, the antibody may be a monoclonal antibody. In one example, the term antibodies may be loosely interpreted to include intact antibodies, antibody fragments, and antigen binding fragment, as long as they exhibit the desired biological activity.

A typical immunoglobulin (antibody) structural unit, as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CHI, CH2 and CH3). In one example, the antibody may comprise full length antibody, which when used referred to an antibody that contains two heavy chains and two light chains, and optionally associated by disulfide bonds as occurs with naturally-produced antibodies.

In one example, the antibody as described herein may be produced by a cell. In one example, the antibody as described herein may be produced by chemical synthesis. In one example, the antibody as described herein may be derived from a mammal. In one example, the antibody as described herein may be derived from an animal such as, but not limited to, mouse, rat, horse, pig, or goat. In one example, the antibody as described herein may be produced using a recombinant cell culture system. In one example, the antibody as described herein may be a purified antibody (for example, by immune-affinity chromatography). In one example, the antibody as described herein may be a human antibody. In one example, the antibody as described herein may be a humanized antibody (antibody from non-human species whose protein sequences have been modified to increase their similarity to antibody variants produced naturally in humans). In one example, the antibody as described herein may be a chimeric antibody (antibody made by combining genetic material from a non-human source, e.g., mouse, rat, horse, or pig, with genetic material from humans). In one example, the antibody as described herein may be multispecific antibody.

As used herein, the term "isolated" refers to a substance and/or entity that has been separated from at least some of the components with which it was associated when initially produced (whether in nature and/or in an experimental setting), and/or produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In one example, the isolated antibodies may be about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (for example, buffer, solvent, water, and the like).

At the same time, the phrase "antigen binding fragment", as used herein, includes a portion of an intact antibody, such as, for example, the antigen-binding or variable region of an antibody. For example, antigen binding fragment may include, but is not limited to, Fab fragment, Fab 1 fragment, F(ab'), fragment, Fv fragment, diabody, a single-chain antibody molecule, triabodies, tetrabodies, linear antibodies, and multispecific antibodies formed from antibody fragments. For example, antibody fragments include isolated include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In one example, the antigen binding fragment as described herein contains sufficient sequence of the parent antibody of which it is a fragment that it binds to the same antigen as does the parent antibody. In one example, the antigen binding fragment as described herein binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

The antibody as described herein may be a member of any immunoglobulin class, including, but is no limited to, any of the classes known in the art, for example, IgG, IgM, IgA, and IgD. In one example, the antibodies as described herein may be an IgG antibody. In one example, the antibodies as described herein may be any one of the IgG antibody, including, but is not limited to, an IgG1 antibody, an IgG2 antibody, an IgG3 antibody, an IgG4 antibody, and the like. In one example, the antibodies as described herein may be an IgG1 antibody.

As used herein, the term "about" as used herein to one or more values of interest, refers to a value that is similar to a stated reference value. In some examples, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%), or less in either direction (greater than or less than) of the stated reference value unless otherwise stated or otherwise evident from the context (except where such number would exceed 100% of a possible value).

In one example, SEQ ID NO: 3 encodes the heavy chain CDR1 of 3C H5L1 antibody, which comprises GYTFTSNY (SEQ ID NO: 3). In one example, SEQ ID NO: 4 encodes the heavy chain CDR2 of 3C H5L1 antibody, which comprises INPRGGST (SEQ ID NO: 4). In one example, SEQ ID NO: 5 encodes the heavy chain CDR3 of 3C H5L1 antibody, which comprises ARGGRALFYD-SYTTPRDGGSWWFDP (SEQ ID NO: 5). The sequence identifier described herein referred to sequences described in FIG. 21.

In one example, the isolated antibody, or antigen binding fragment thereof, wherein the antibody comprises at least: one light chain amino acid sequences comprising at least one CDR selected from the group consisting of: (a) a CDRL1 as shown in SEQ ID NO: 6, or a CDRL1 sequence having at least 70% sequence identity to SEQ ID NO: 6 therefrom, (b) a CDRL2 as shown in SEQ ID NO: 7, or a CDRL2 sequence having at least 70% sequence identity to SEQ ID NO: 7 therefrom, (c) a CDRL3 as shown in SEQ ID NO: 8, or a CDRL3 sequence having at least 70% sequence identity to SEQ ID NO: 8 therefrom, or an antibody, or antigen binding fragment thereof.

In one example, SEQ ID NO: 6 encodes the light chain CDR1 of 3C H5L1 antibody, which comprises QDIRKY (SEQ ID NO: 6). In one example, SEQ ID NO: 7 encodes the light chain CDR2 of 3C H5L1 antibody, which comprises DAS (SEQ ID NO: 7). In one example, SEQ ID NO: 8 encodes the light chain CDR3 of 3C H5L1 antibody, which comprises QQFDDLPIT (SEQ ID NO: 8). The sequence identifier described herein referred to sequences described in FIG. 21.

In one example, the antibody, or antigen binding fragment thereof, as described herein comprises at least one heavy chain amino acid sequences comprising at least one CDR selected from the group consisting of (a) a CDRH1 as shown in SEQ ID NO: 3, or a CDRH1 sequence having at least 70% sequence identity to SEQ ID NO: 3 therefrom, (b) a CDRH2 as shown in SEQ ID NO: 4, or a CDRH2 sequence having at least 70% sequence identity to SEQ ID NO: 4 therefrom, (c) a CDRH3 as shown in SEQ ID NO: 5, or a CDRH3 sequence having at least 70% sequence identity to SEQ ID NO: 5 therefrom, and at least one light chain amino acid sequences comprising at least one CDR selected from the group consisting of (d) a CDRL1 as shown in SEQ ID NO: 6, or a CDRL1 sequence having at least 70% sequence identity to SEQ ID NO: 6 therefrom, (e) a CDRL2 as shown in SEQ ID NO: 7, or a CDRL2 sequence having at least 70% sequence identity to SEQ ID NO: 7 therefrom, (f) a CDRL3 as shown in SEQ ID NO: 8, or a CDRL3 sequence having at least 70% sequence identity to SEQ ID NO: 8 therefrom, or an antibody, or antigen binding fragment thereof, recognizing a whole dengue virus particle.

In one example, the antibody, or antigen binding fragment, as described herein may comprise at least one, at least two, or all of the heavy chain amino acid sequences comprising the CDR as described herein. In one example, the antibody, or antigen binding fragment, as described herein may comprise at least one, at least two, or all of the light chain amino acid sequences comprising the CDR as described herein.

As used herein, the term "CDR" or "complementarity determining region" refers to the amino acid sequence that encodes for the one or more structural elements of an antibody or antigen binding fragment thereof. In one example, the antibody, or antigen binding fragment thereof, may comprises a polypeptide whose amino acid sequence includes at least one CDR (e.g., at least one heavy chain CDR and/or at least one light chain CDR) that is substantially identical to one found in a reference antibody. In one example, the antibody, or antigen binding fragment thereof, the included CDR may be substantially identical to a reference CDR in that it is either identical in sequence or contains between 1, or 2, or 3, or 4, or 5 amino acid substitutions as compared with the reference CDR. In one example, the included CDR may be substantially identical to a reference CDR in that it shows at least 70%, or at least 75%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity with the reference CDR. In one examples, the included CDR may be substantially identical to a reference CDR in that it shows at least 95%, or at least 96%, or at least 97%, or at least 98%, or at least 99%, or 100% sequence identity with the reference CDR. In one example, the included CDR may be substantially identical to a reference CDR in that at least one, or at least two, amino acid within the included CDR is deleted, added, or substituted as compared with the reference CDR but the included CDR has an amino acid sequence that is otherwise identical with that of the reference CDR. In one example, the included CDR may be substantially identical to a reference CDR in that 1, or 2, or, 3, or 4, or 5 amino acids within the included CDR are deleted, added, or substituted as compared with the reference CDR but the included CDR has an amino acid sequence that is otherwise identical to the reference CDR. In one example, the included CDR may be substantially identical to a reference CDR in that at least one amino acid within the included CDR is substituted as compared with the reference CDR but the included CDR has an amino acid sequence that is otherwise identical with that of the reference CDR. In one example, the antibody, or antigen binding fragment, as described herein may comprise a polypeptide whose amino acid sequence includes structural elements recognized by those skilled in the art as an immunoglobulin variable domain. In one example, the antibody, or antigen binding fragment, as described herein may be a polypeptide protein having a binding domain which is homologous or largely homologous to an immunoglobulin-binding domain. As would be appreciated to the skilled person in the art, an antibody is made of two light chains and two heavy chains each comprising variable regions and constant regions. The light chain variable region comprises 3 CDRs, identified herein as CDRL1, CDRL2, and CDRL3 flanked by framework regions. The heavy chain variable region comprises 3 CDRs, identified herein as CDRH1, CDRH2, and CDRH3 flanked by framework regions.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

In one example, the isolated antibody, or antigen binding fragment thereof, as described herein may comprises at least: one, or two or all heavy chain amino acid sequences comprising at least one CDR selected from the group consisting of (a) a CDRH1 as shown in SEQ ID NO: 3, or a CDRH1 sequence having at least 70%, or at least 80%, or at least 85%, or at least 90%, or at least 95% sequence identity to SEQ ID NO: 3 therefrom, (b) a CDRH2 as shown in SEQ ID NO: 4, or a CDRH2 sequence having at least 70%, or at least 80%, or at least 85%, or at least 90%, or at least 95% sequence identity to SEQ ID NO: 4 therefrom, (c) a CDRH3 as shown in SEQ ID NO: 5, or a CDRH3 sequence having at least 70%, or at least 80%, or at least 85%, or at least 90%, or at least 95% sequence identity to SEQ ID NO: 5 therefrom, and/or at least one, or two or all light chain amino acid sequences comprising at least one CDR selected from the group consisting of (a) a CDRL1 as shown in SEQ ID NO: 6, or a CDRL1 sequence having at least 70%, or at least 80%, or at least 85%, or at least 90%, or at least 95% sequence identity to SEQ ID NO: 6 therefrom, (b) a CDRL2 as shown in SEQ ID NO: 7, or a CDRL2 sequence having at least 70%, or at least 80%, or at least 85%, or at least 90%, or at least 95% sequence identity to SEQ ID NO: 7 therefrom, (c) a CDRL3 as shown in SEQ ID NO: 8, or a CDRL3 sequence having at least 70%, or at least 80%, or at least 85%, or at least 90%, or at least 95% sequence identity to SEQ ID NO: 8 therefrom, or an antibody, or antigen binding fragment thereof, recognizing a whole dengue virus particle.

In one example, the isolated antibody, or antigen binding fragment thereof, as described herein may comprise at least one heavy chain amino acid sequences comprising at least one CDR selected from the group consisting of (a) a CDRH1 as shown in SEQ ID NO: 3, or a CDRH1 sequence differing 1 or 2 amino acids therefrom, (b) a CDRH2 as shown in SEQ ID NO: 4, or a CDRH2 sequence differing 1 or 2 amino acids therefrom, (c) a CDRH3 as shown in SEQ ID NO: 5, or a CDRH3 sequence differing 1 or 2 amino acids therefrom, and/or at least one light chain amino acid sequences comprising at least one CDR selected from the group consisting of (a) a CDRL1 as shown in SEQ ID NO: 6, or a CDRL1 sequence differing 1 or 2 amino acids therefrom, (b) a CDRL2 as shown in SEQ ID NO: 7, or a CDRL2 sequence differing 1 or 2 amino acids therefrom, (c) a CDRL3 as shown in SEQ ID NO: 8, or a CDRL3 sequence differing 1 or 2 amino acids therefrom, or an antibody, or antigen binding fragment thereof, recognizing a whole dengue virus particle.

In one example, the isolated antibody, or antigen binding fragment thereof, as described herein may comprise at least one, or two or all heavy chain amino acid sequences comprising at least one CDR selected from the group consisting of (a) a CDRH1 as shown in SEQ ID NO: 3, or a CDRH1 sequence differing 1 or 2 amino acids therefrom, (b) a CDRH2 as shown in SEQ ID NO: 4, or a CDRH2 sequence differing 1 or 2 amino acids therefrom, (c) a CDRH3 as shown in SEQ ID NO: 5, or a CDRH3 sequence differing 1 or 2 amino acids therefrom, and/or at least one, or two or all light chain amino acid sequences comprising at least one CDR selected from the group consisting of (a) a CDRL1 as shown in SEQ ID NO: 6, or a CDRL1 sequence differing 1 or 2 amino acids therefrom, (b) a CDRL2 as shown in SEQ ID NO: 7, or a CDRL2 sequence differing 1 or 2 amino acids therefrom, (c) a CDRL3 as shown in SEQ ID NO: 8, or a CDRL3 sequence differing 1 or 2 amino acids therefrom, or an antibody, or antigen binding fragment thereof, recognizing a whole dengue virus particle.

In one aspect, there is provided an isolated antibody, or antigen binding fragment thereof, wherein the antibody comprises or consist of heavy chain amino acid sequence comprising all of the CDR selected from the group consisting of (a) a CDRH1 as shown in SEQ ID NO: 3, (b) a CDRH2 as shown in SEQ ID NO: 4, and (c) a CDRH3 as shown in SEQ ID NO: 5, recognizing a whole dengue virus particle.

In another aspect, there is provided an isolated antibody, or antigen binding fragment thereof, wherein the antibody comprises or consist of light chain amino acid sequence comprising all of the CDR selected from the group consisting of (a) a CDRL1 as shown in SEQ ID NO: 6, (b) a CDRL2 as shown in SEQ ID NO: 7, (c) a CDRL3 as shown in SEQ ID NO: 8, recognizing a whole dengue virus particle.

In yet another aspect, there is provided an isolated antibody, or antigen binding fragment thereof, wherein the antibody comprising or consisting of heavy chain amino acid sequence comprising all of the CDR selected from the group consisting of (a) a CDRH1 as shown in SEQ ID NO: 3, (b) a CDRH2 as shown in SEQ ID NO: 4, (c) a CDRH3 as shown in SEQ ID NO: 5, and light chain amino acid sequence comprising all of the CDR selected from the group consisting of (a) a CDRL1 as shown in SEQ ID NO: 6, (b) a CDRL2 as shown in SEQ ID NO: 7, (c) a CDRL3 as shown in SEQ ID NO: 8, recognizing a whole dengue virus particle.

Figure 2:
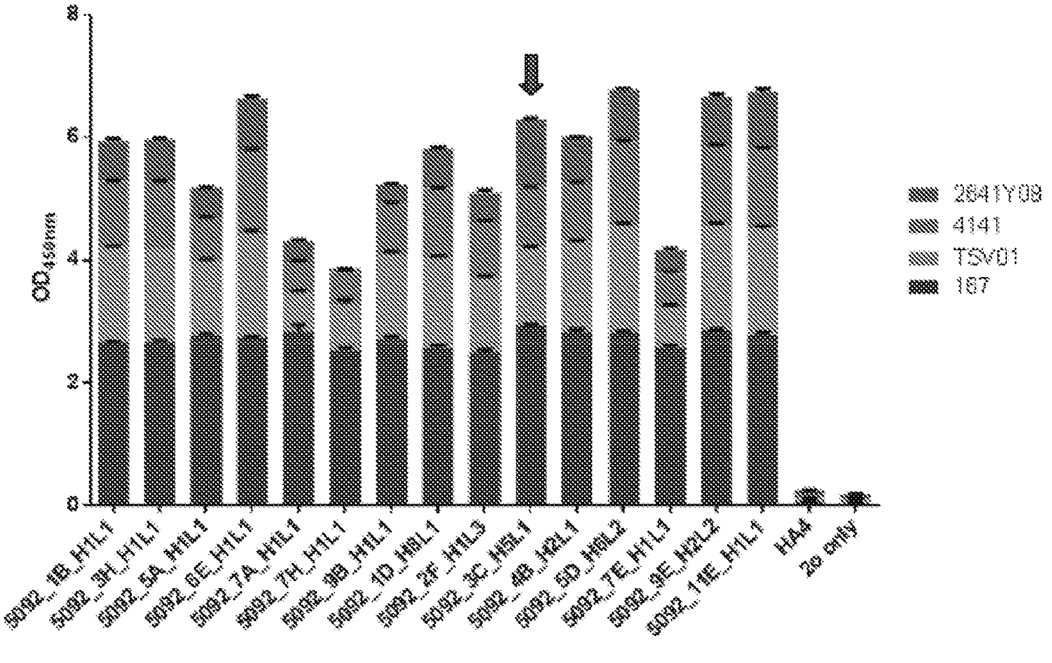
FIG. 2 shows a bar graph showing the binding capacity of various antibody clones on live viral particles as assayed by ELISA. Different viral particles are depicted in descending order, where 2641Y08 (top most bar) is a DENV-4 virus particle, 4141 (second bar from top) is a DENV-3 virus particle, TSV01 (third bar from top) is a DENV-2 virus particle, and 167 (bottom bar) is a DENV-1 virus particle. Binding profile of 3C H5L1 antibody is highlighted with arrow. Thus.
Figure 3:
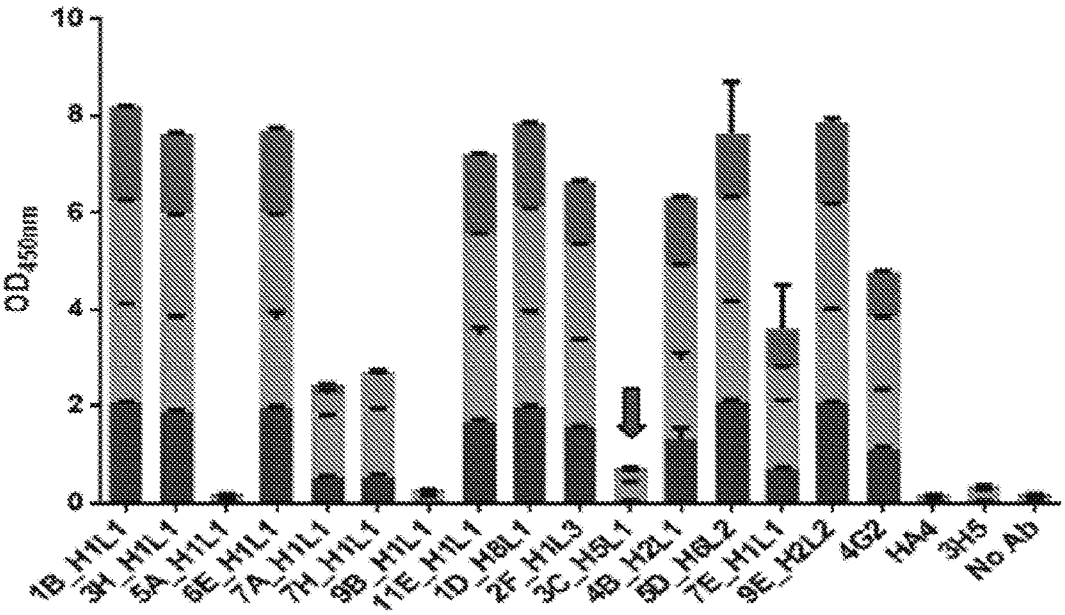
FIG. 3 shows a bar graph showing the binding capacity of various antibody clones towards recombinant E protein as assayed by ELISA. As highlighted by the arrow pointing down, binding of 3C H5L1 to recombinant E protein of all 4 DENV serotypes was very weak. Thus, FIG. 3 (as well as FIG. 1 and FIG. 2) shows that the epitope of 3C H5L1 antibody is more prominently displayed on whole viral particles, particularly when alive.
Figure 6:
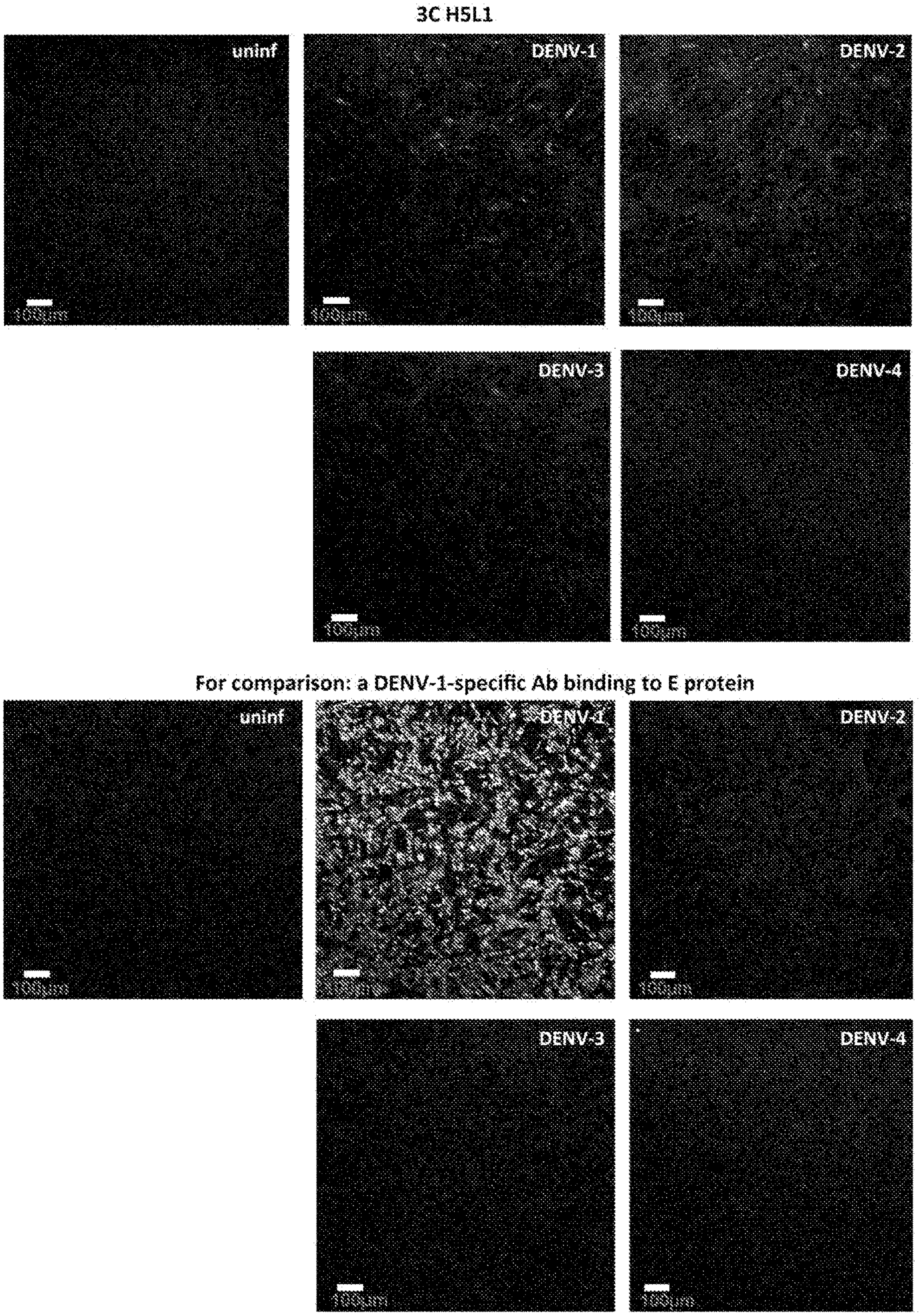
FIG. 6 shows immunohistochemistry images of BHK-21 cells (i.e. fibroblast cells) stained with 3C H5L1 antibody and an E protein-specific human monoclonal antibody for comparison. BHK-21 cells were infected for 24 hours and fixed before staining with the respective antibodies. As illustrated by the dark immunohistochemistry images, 3C H5L1 antibody showed weak staining for DENV-1, 2 and 3, and no staining for DENV-4. Infected cells produce large amounts of E protein in the endoplasmic reticulum (ER) and antibodies specific for E protein therefore produce a very bright stain (see lower panels showing staining of a control antibody binding to E-protein). As 3C H5L1 only weakly binds to E protein, the observed bright stain is probably the result of detection of whole virus particles binding to the cell surface or the detection of newly produced virus particles inside the cells, before being released. The scale bars in the graphs indicate 100 μm. Thus, FIG. 6 confirms 3C H5L1 antibody preferentially binds to intact virus particles and only binds weakly to E protein.

As illustrated in the experimental section, as exemplified in FIG. 2, FIG. 3, and FIG. 6, the inventors found the antibody, or antigen binding fragment thereof, as described herein is capable of binding to a whole dengue virus particle. For example, FIG. 3 shows the antibody as described herein cannot bind efficiently to any of the recombinant E protein of the 4 DENV serotypes. In contrast, as shown in FIG. 2 and FIG. 6, the antibody as described herein binds to all four DENV virus particles. Thus, in one example, the antibody, or antigen binding fragment thereof, as described herein, is capable of binding to a whole dengue virus particle better than binding to a (recombinant soluble monomeric) dengue virus surface glycoprotein. In one example, the antibody, or antigen binding fragment, as described herein may not bind well to the monomeric dengue virus surface glycoprotein, which is an E protein.

As known in the art, the dengue virus (or DENV) has four genetically and antigenically related viral serotypes, designated as DENV-1, DENV-2, DENV-3 and DENV-4. The inventors of the present disclosure found that the antibody, or antigen binding fragment, as described herein, could surprisingly bind to and neutralize multiple dengue virus serotypes. For example, in FIG. 2, the antibody as described herein could bind to all four DENV serotypes. Thus, in one example, the antibody, or antigen binding fragment thereof, as described herein, is capable of binding to and/or neutralizing at least one dengue virus particle. In one example, the dengue virus particle may be at least one, or at least two, or at least three, or all of the dengue virus selected from the group consisting of DENV serotype 1 (DENV-1), DENV serotype 2 (DENV-2), DENV serotype 3 (DENV-3), and DENV serotype 4 (DENV-4). In one example, the dengue virus particle may be at least one, or at least two, or all of the dengue virus selected from the group consisting of DENV serotype 1 (DENV-1), DENV serotype 2 (DENV-2) and DENV serotype 3 (DENV-3). In one example, the dengue virus particle may be at least one, or both, dengue virus selected from the group consisting of DENV serotype 1 (DENV-1) and DENV serotype 2 (DENV-2). Amongst all DENV serotypes, the antibody was found to neutralize DENV-2 serotype most efficiently. Thus, in one example, the dengue virus may be DENV serotype 2 (DENV-2). In general, a "serotype" refers to distinct variations within a species of bacteria or viruses or among immune cells of different individuals.

In one example, the antibody, or antigen binding fragment thereof, as described herein comprises or consists of a heavy chain variable region encoded by a nucleotide sequence having at least 65%, or at least 70%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity to SEQ ID NO: 1. In one example, the antibody, or antigen binding fragment thereof, as described herein comprises or consists of a heavy chain variable region encoded by the nucleotide sequence SEQ ID NO: 1. In one example, SEQ ID NO: 1 is the nucleotide sequence which encodes for the 3C H5L1 heavy chain variable region, which comprises the sequence as follows:

```
                                          (SEQ ID NO: 1)
GAGGTCCAGCTGGTACAGTCTGGGCCTGACGTCGAGAAGCCTGGGGCCTC

AGTGAAGGTTTCCTGCAAGGCATCTGGATACACCTTCACCAGCAACTATA

TACACTGGGTGCGACAGGCCCCTGGACAAGGGCTTGAGTGGATGGGGGTA

ATCAACCCTAGGGGTGGTAGCACAGCCAGCGCACAGAAATTCCAGGGAAG

AATCACCATGACCAGGGACACGTCCACGAGCACAGTTTACATGGAACTGA

GCAGCCTGAGATCTGACGACACGGCCGTGTATTACTGTGCGAGAGGGGGA

AGGGCCCTTTTCTATGATAGTTACACGACCCCCCGAGACGGAGGGTCGTG

GTGGTTCGACCCCTGGGGCCAGGGAAGCCTGGTCACCGTCTCCTCA.
```

In one example, the antibody, or antigen binding fragment thereof, as described herein comprises or consists of a light chain variable region encoded by the nucleotide sequence having at least 65%, or at least 70%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% sequence identity to SEQ ID NO: 2.

In one example, the antibody, or antigen binding fragment thereof, as described herein comprises or consists of a light chain variable region encoded by the nucleotide sequence SEQ ID NO: 2. In one example, SEQ ID NO: 2 is the nucleotide sequence which encodes for the 3C H5L1 light chain, which comprises the sequence as follows:

(SEQ ID NO: 2)
GACATCCAGTTGACCCAGTCTCCATCTTCCCTGTCTGCATCTGTAGGAGA
CAGAGTCACCTTCACTTGCCAGGCGAGCCAGGACATTAGGAAGTATTTAA
ATTGGTATCAGCAGAAACCAGGGAAAGCCCCTAAACTCCTAATCTACGAT
GCATCCAATTTGAAAACAGGGGTCCCATCAAGGTTCAGTGGAAGTGGATC
TGGGACAGATTTTACTTTCACCATCAGCAGCCTGCAGCCTGAAGATGTTG
CAACATACTACTGTCAACAGTTTGATGATCTCCCGATCACCTTCGGCCAG
GGGACACGACTGCAGATTAAACGA.

In one example, the antibody, or antigen binding fragment thereof, as described herein comprises or consists of a heavy chain variable region encoded by the nucleotide sequence SEQ ID NO: 1 and a light chain variable region encoded by the nucleotide sequence SEQ ID NO: 2.

In one example, the antibody, or antigen binding fragment thereof, as described herein comprises a heavy chain variable region comprising or consisting of the amino acid sequence of SEQ ID NO: 9, or an amino acid sequence having a sequence identity of at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% thereto. In one example, the heavy chain variable region comprises the amino acid sequence:

(SEQ ID NO: 9)
EVQLVQSGPDVEKPGASVKVSCKASGYTFTSNYIHWVRQAPGQGLEWMGV
INPRGGSTASAQKFQGRITMTRDTSTSTVYMELSSLRSDDTAVYYCARGG
RALFYDSYTTPRDGGSWWFDPWGQGSLVTVSS.

In one example, the antibody, or antigen binding fragment thereof, as described herein comprises of a light chain variable region comprising or consisting of the amino acid sequence of SEQ ID NO: 10, or an amino acid sequence having a sequence identity of at least 85% or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% thereto. In one example, the light chain variable region comprises the amino acid sequence:

(SEQ ID NO: 10)
DIQLTQSPSSLSASVGDRVTFTCQASQDIRKYLNWYQQKPGKAPKLLIYD
ASNLKTGVPSRFSGSGSGTDFTFTISSLQPEDVATYYCQQFDDLPITFGQ
GTRLQIK.

In one example, the antibody, or antigen binding fragment thereof, as described herein comprises or consist of a heavy chain variable region comprising or consisting of the amino acid sequence of SEQ ID NO: 9 and a light chain variable region comprising or consisting of the amino acid sequence of SEQ ID NO: 10.

Figure 4:
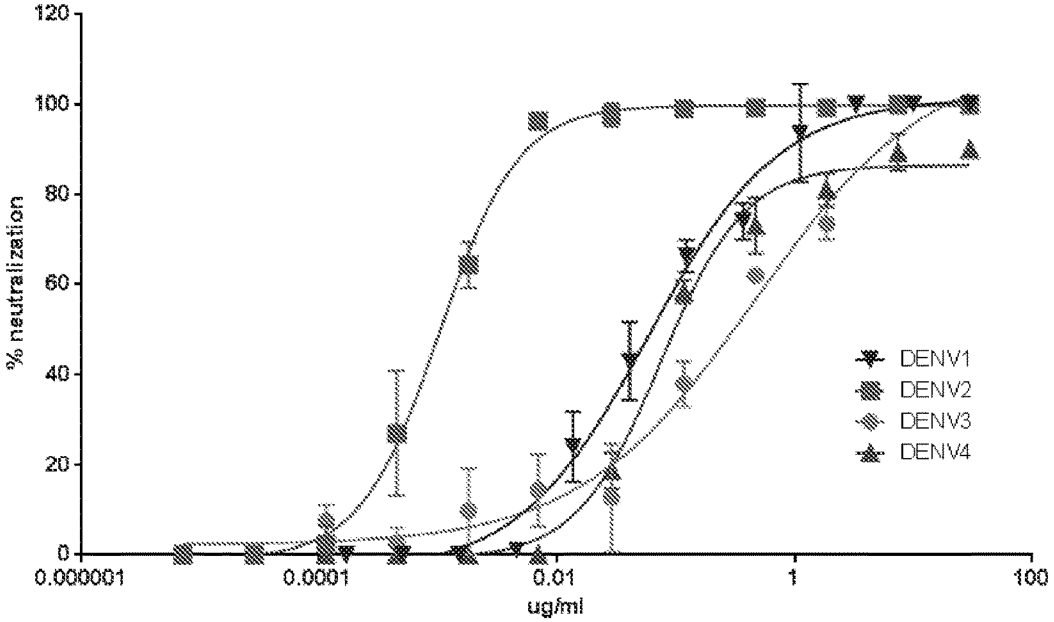
FIG. 4 shows a line graph showing the results of a plaque reduction neutralization assay/test (PRNT) of 3C H5L1 antibody with BHK-21 cells (i.e. fibroblast cells). The virus strains used were DENV-1 167, DENV-2 TSV01, DENV-3 VN32/96 and DENV-4 2641Y08.
Figure 5:
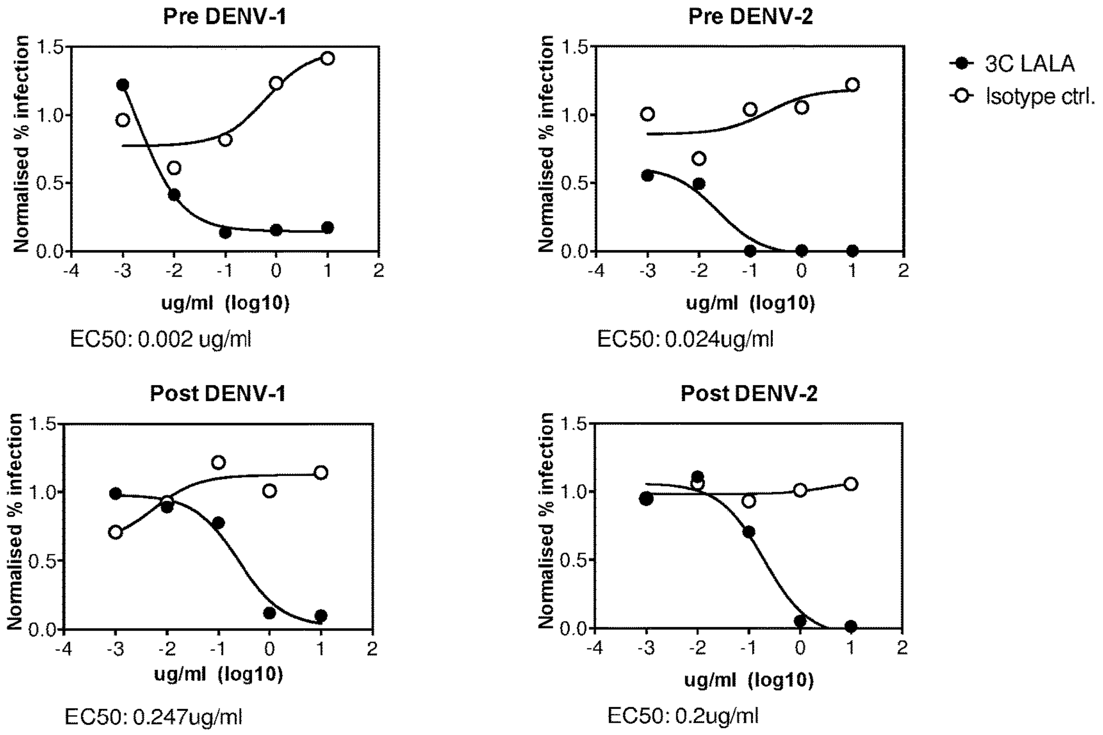
FIG. 5 shows line graphs showing the results of the pre- and post-attachment neutralization assay of virus and Fc-modified 3C H5L1 antibody (3C H5L1 with a LALA mutation, named 3C LALA in FIG. 5). For the pre-attachment neutralization assay, virus and modified 3C H5L1 antibody were mixed before the mixture was added to U937-DC-SIGN (i.e. monocyte-like human cell line U937 expressing DC-SIGN) cells for infection. For the post-attachment neutralization assay, virus was first incubated with the cells at 4° C. (to avoid fusion and internalization of the virus). Virus was then washed away, and modified 3C H5L1 antibody was added before incubating the cells at 37° C. to initiate infection. 08K3126 (i.e. DENV-1 virus) and TSV01 (i.e. DENV-2 virus) were used for the assay. Thus.
Figure 7:
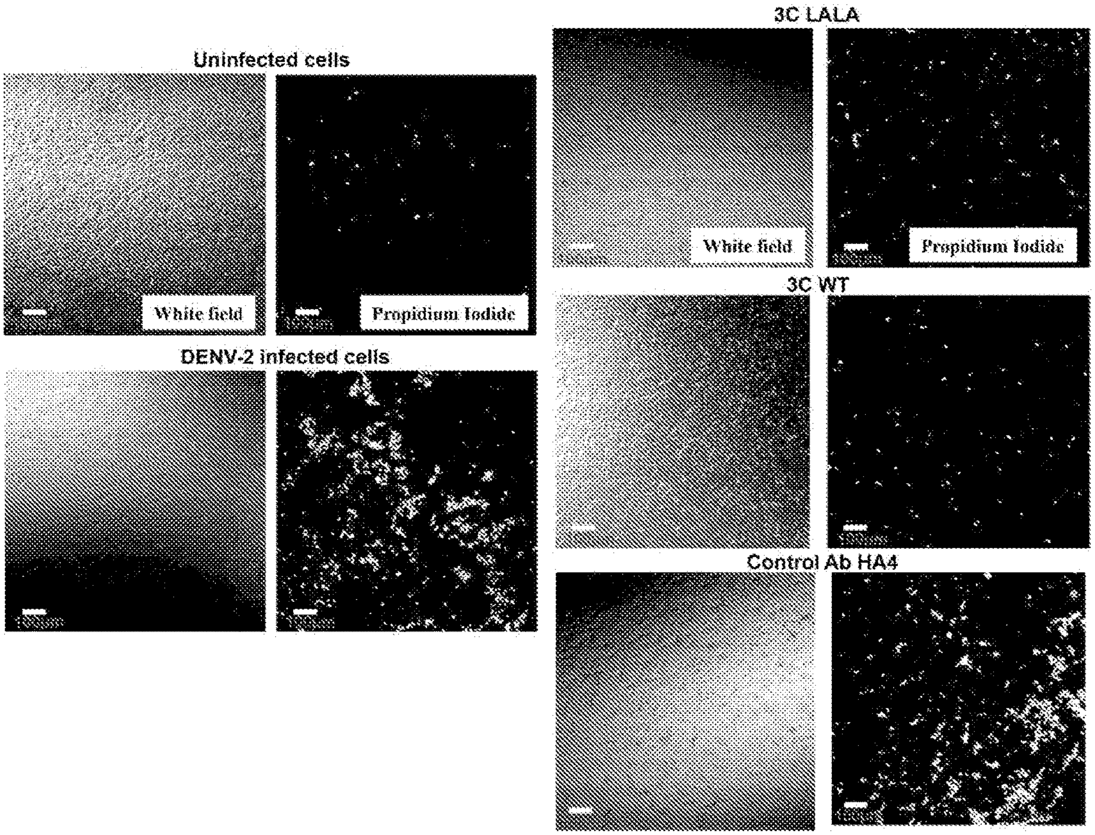
FIG. 7 shows a series of confocal microscopy images of cells in fusion inhibition assay. 10 μg/ml antibodies (modified (3C-LALA)—top right panels; wild type (WT)—middle right panels; and control antibodies—bottom right panels) were added to infected C6/36 cells (i.e. *Aedes albopictus* clone). Fusion was then triggered by adding an acidic buffer. After removing the virus, cells were washed, stained with propidium iodide (PI) and imaged immediately, using a confocal microscope. PI stains fused cells and individual dead cells. The clusters of nuclei stained with PI represent clusters of fused cells. White field images of the cells are shown as a reference for the actual number of cells in the microscope field. A 10× magnification objective was used. Top left panels show very little propidium iodide (PI) staining in uninfected cells (i.e. very little bright spots). In contrast, bottom left panels showed cells infected with DENV-2 shows a significant number of cells stained positive for propidium iodide (i.e. bright spots). Right panels of FIG. 7 (labelled with 3C-LALA and 3C-WT) showed little propidium iodide staining. In contrast, bottom right panels of FIG. 7 (labelled with control antibody HA4) showed many cells stained positive for propidium iodide. The scale bars in the graphs indicate 100 μm. Thus.
Figure 8:
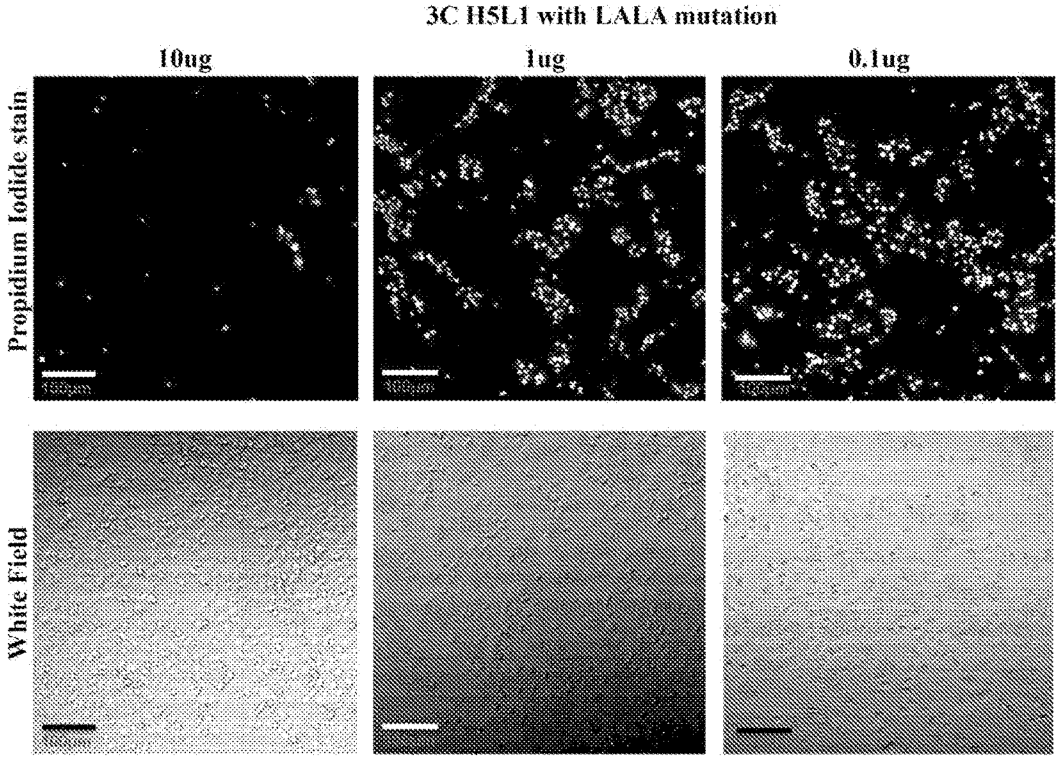
FIG. 8 shows a series of confocal microscopy images of cells in fusion inhibition assay using varying concentrations of modified 3C antibody. In the assay, 10 μg/ml, 1 μg/ml and 0.1 μg/ml of modified 3C antibody (i.e. 3C-LALA) were used. Top panels showed a trend for a direct relationship between the concentration and the inhibition of fusion in cells, where cells treated with 10 μg/ml has very little propidium iodide positive cells, 1 μg/ml has more propidium iodide positive cells (as compared to 10 μg/ml) and 0.1 μg/ml has more propidium iodide positive cells (as compared to 1 g/ml). A 20× magnification objective was used. The scale bars in the graphs indicate 100 μm. Thus.
Figure 9:
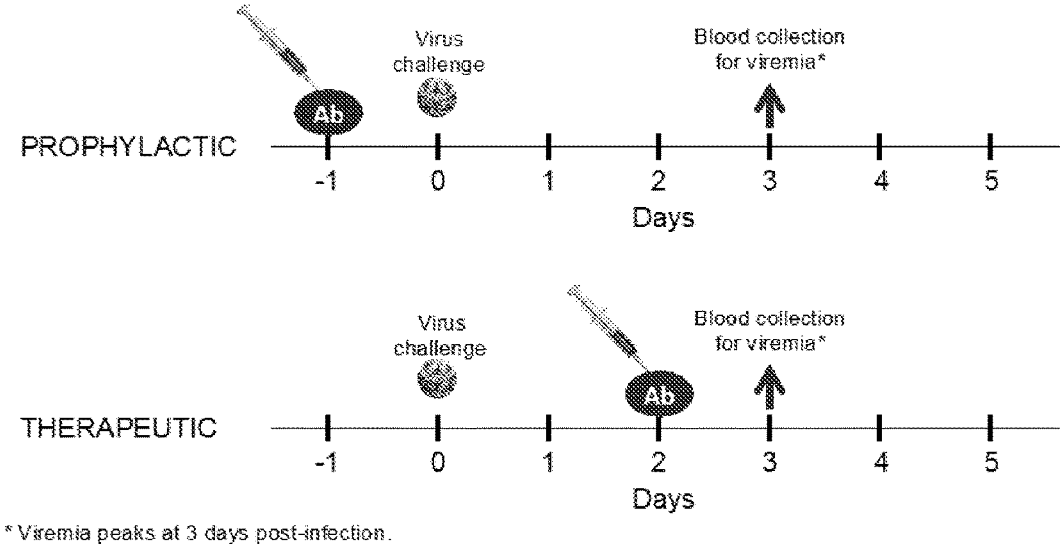
FIG. 9 shows schematic diagrams of the experimental plans for in vivo efficacy tests in either AG129 or IFNAR mouse models. Time points of antibody transfer and virus challenge in the prophylactic and therapeutic models are depicted with reference to the number of days pre- or post-challenge. Antibody was injected intravenously whereas virus was injected intraperitoneally.
Figure 10:
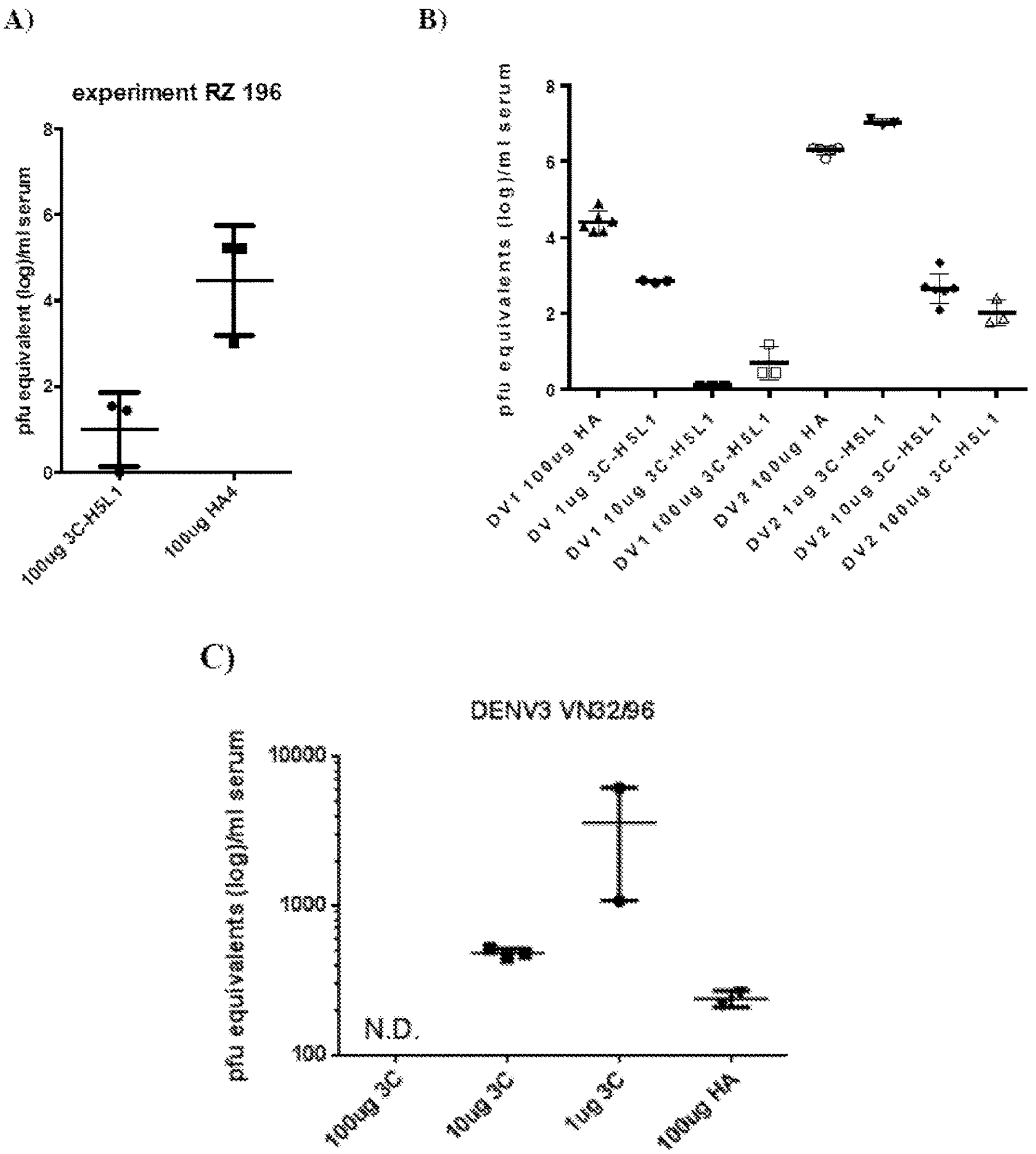
FIG. 10 shows dot plots depicting the results of pre-infection (i.e. prophylactic) treatment of 3C H5L1 antibody in mice. 100 μg or 10 μg of 3C H5L1 monoclonal antibody (mAb) or 100 μg of a control human mAb HA4 were injected intravenously (i.v.) into AG129 mice. 24 h later mice were infected with $5\times10^6$ pfu DENV-1, DENV-2, or DENV-3. At day 3 after infection, which is the peak of viremia, blood was collected from mice and virus was detected by qRT-PCR and standardized as pfu equivalent/ml serum by including a virus stock with known pfu/ml in the realtime PCR. Plaque forming units (pfu) are equivalent to infectious virus particles and are determined in a plaques assay. In particular, A) shows dot plot of infection detected (as measured in pfu equivalents/ml serum) in mice infected with DENV-2 strain TSV01 after mAb transfer; B) shows the dot plot of infection detected (as measured in pfu equivalents/ml serum) in mice infected after mAb transfer with DENV-2 strain D2Y98P or DENV-1 strain 08K3126, respectively; and C) shows the dot plot of infection detected (as measured in pfu equivalents/ml serum) of mice infected with DENV-3 (VN32/96 strain). In mice treated with 100 μg of 3C H5L1 monoclonal antibody, no viremia was detected (N.D.) at day 3 after infection (see FIG. 10C, most left item in x-axis). Thus.
Figure 11:
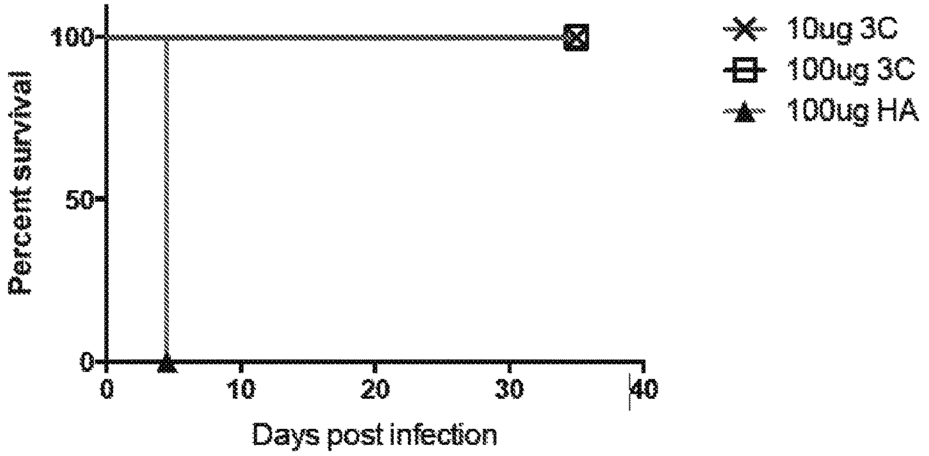
FIG. 11 shows the survival curve of mice up to at least 30 days post infection. Mice received either 3C H5L1 (i.e. 3C) antibody or control HA4 (i.e. HA) antibody 24 hours before infection with $1\times10^7$ pfu DENV-2 strain D2Y98P (injected intraperitoneally) and monitored for their survival.

As shown in the Experimental Section as described herein, antibodies towards DENV virus can neutralizes, inhibit virus uptake in cells (i.e. inhibit virus fusion to target cells), as well as provide prophylactic protection against DENV infection (see for example FIG. 4 and FIG. 5 for neutralization assay, FIG. 7 and FIG. 8 for fusion inhibition assay, and FIG. 9 to FIG. 11 for in vivo prophylactic assays). However, as known in the art, some antibodies (known in the art) could cause the severe clinical manifestation of DENV infection. For example, antibodies known in the art have been known to cause antibody-dependent enhancement (ADE), which describes the unwanted increase in the efficiency of virus infection. Antibody-dependent enhancement has been known to occur when dengue infection occurs in the presence of non-neutralising or sub-neutralising concentrations of DENV serotype cross-reactive antibodies known in the art. In antibody-dependent enhancement phenomenon, the antibody-virus complex attaches to the Fc receptors on circulating antigen-presenting cells including dendritic cells, macrophages and monocytes, which allows DENV to replicate in the Fc receptor-bearing cells and achieve higher systemic titers compared to DENV that is not complexed to antibody. The overall outcomes lead to the potential for more severe manifestation of dengue fever.

To avoid the antibody-dependent enhancement, modifications abolishing the potential binding of antibody to Fc receptors may be provided. In one example, the antibody, or antigen binding fragment thereof, as described herein may be a modified IgG1 antibody, or a modified IgG2 antibody, or a modified IgG3 antibody, or a modified IgG4 antibody. In one example, the modification may increase the antibody stability in vivo. In one example, the antibody, or antigen binding fragment thereof, as described herein may have a modification that abolishes the binding of antibodies to Fc-gamma-receptors (FcγR). Without wishing to be bound by theory, a modification that abolishes the binding of antibodies to Fc-gamma-receptors may be advantageous because a decreased binding to FcR may avoid the phenomenon of ADE (Antibody-dependent enhancement) of infection, which is thought to be mostly mediated by the interaction with FcR. In one example, the LALA mutation may be introduced outside the variable region. In one example, the LALA mutation may be introduced to the Fc binding domain. Exemplary modified antibody non-variable (constant) region with LALA mutation is presented in FIG. 22. In one example, the LALA mutation may be in the non-variable heavy chain region, such as depicted in FIG. 22. In one example, the modified antibody with LALA mutation may have non-variable heavy chain region encoded by the nucleotide sequence SEQ ID NO: 11, or amino acid sequence SEQ ID NO: 12.

In one example, the antibody, or antigen binding fragment thereof, as described herein may have modification including, but not limited to, glycosylation, substitution, mutation, and protein sequence modification. In one example, modification may be a LALA mutation as previously described in the art. It is appreciated that the method of modifying an antibody to comprise a LALA mutation is known in the art and the person skilled in the art would be well conversed to include such modification to the antibody as described herein. In one example, the LALA mutation has been described previously in WO2012130831A1.

Figure 12:
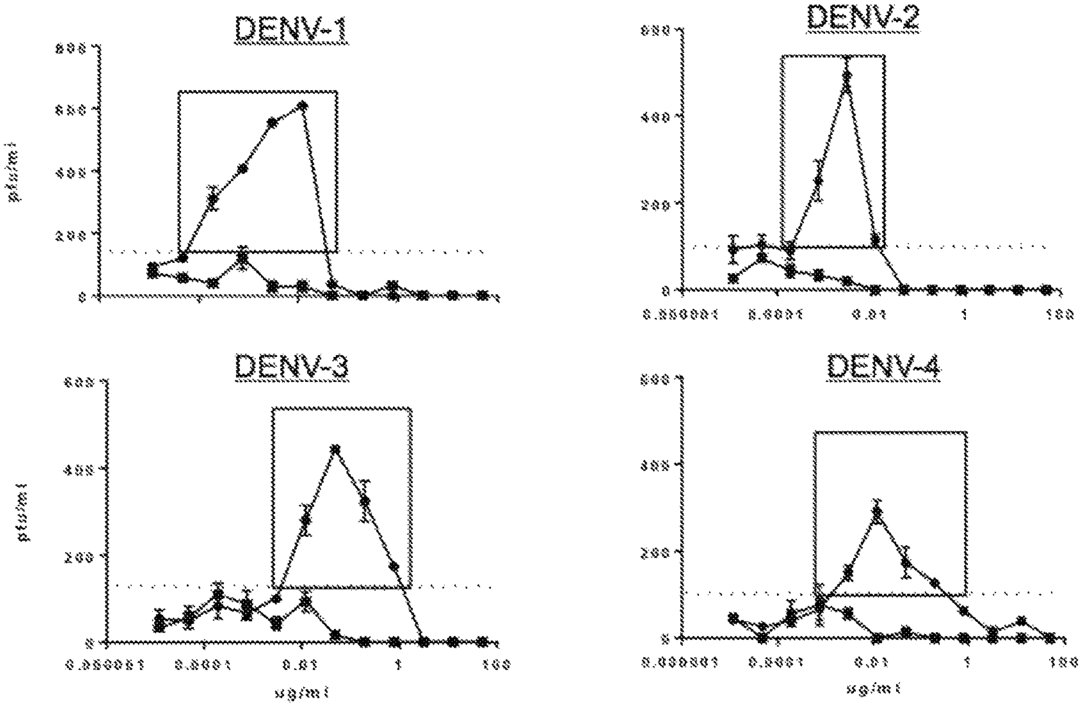
FIG. 12 shows the results of pre-infection treatment (prophylactic) treatment of mice with modified 3C antibody (i.e. LALA mutant of 3C H5L1 antibody). In particular.
Figure 13:
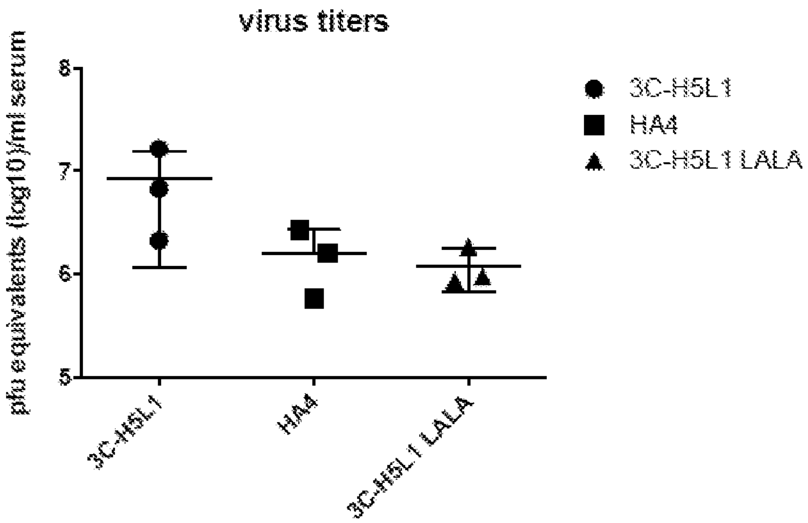
FIG. 13 shows the results of the in vivo validation tests of modified 3C H5L1 antibody (i.e. with LALA mutation). In particular, A) shows the virus titers of mice infected with $1\times10^7$ pfu DENV-2 strain D2Y98P (via intraperitoneal injection) and treated with one of unmodified (wild type) 3C H5L1, or modified 3C H5L1 (i.e. with LALA mutation), or HA4 control antibody 24 hours before infection with DENV2 virus. Virus titres in the blood were analysed three days after infection. The antibody-dependent enhancement (ADE) observed after injection of 1 μg of 3C H5L1 (see also FIG. 10) was reversed when using 1 μg of modified 3C H5L1 (i.e. 3C H5L1 LALA). B) shows the survival curve of mice treated as described in A), wherein mice treated with 1 μg of modified 3C H5L1 (i.e. 3C H5L1 LALA) have a marginal survival advantage over mice treated with 1 μg of unmodified/wild type 3C H5L1. Note that in this validation test, DENV-2 virus used to infect AG129 mice was a very aggressive strain. Thus, mice could only survive when treated with 10 μg of 3C H5L1 or more (see FIG. 11). Thus.
Figure 13:
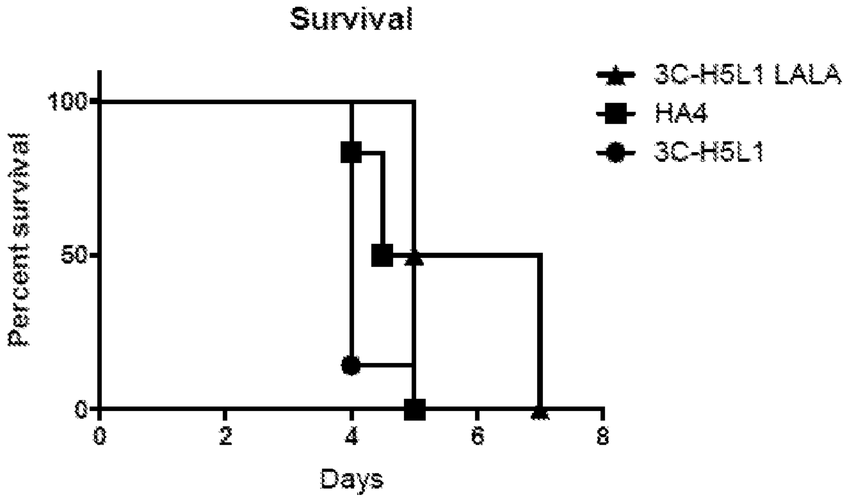
Figure 18:
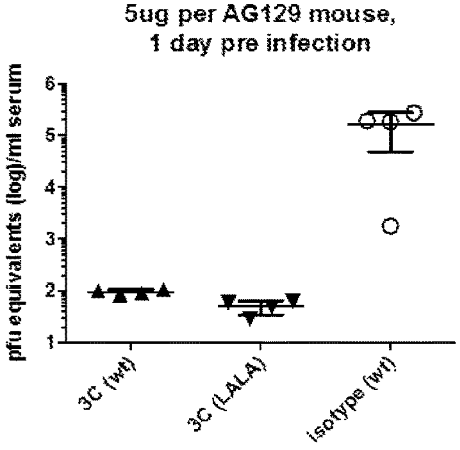
FIG. 18 shows the results into the investigation of the effect of the modification of 3C H5L1 antibody in preventing DENV-2 in vivo in AG129 mice. AG129 mice were treated intravenously (i.v.) with 5 μg of 3C (unmodified/wild type): no Fc mutation, 3C (modified/LALA): LALA mutation in the Fc part, or isotype (wt): isotype control without Fc mutation. One day later mice were infected with DENV-2 D2Y98P intraperitoneally (i.p.). Viremia was measured at day three after infection.
Figure 19:
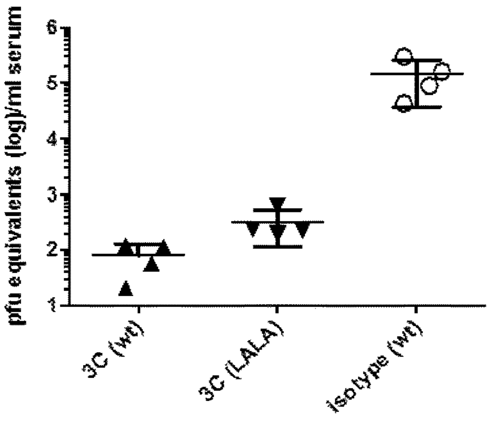
FIG. 19 shows the results into the investigation of the effect of the modification of 3C H5L1 antibody in treating DENV-2 infection in vivo in IFNAR or AG129 mice. IFNAR or AG129 mice were treated intravenously (i.v.) with 100 ug of 3C (unmodified/wild type): no Fc mutation, 3C (modified/LALA): LALA mutation in the Fc part, or isotype (wt): isotype control without Fc mutation two days post infection with DENV-2 D2Y98P injected intraperitoneally (i.p.). Viremia was measured at day three after infection.
Figure 19:
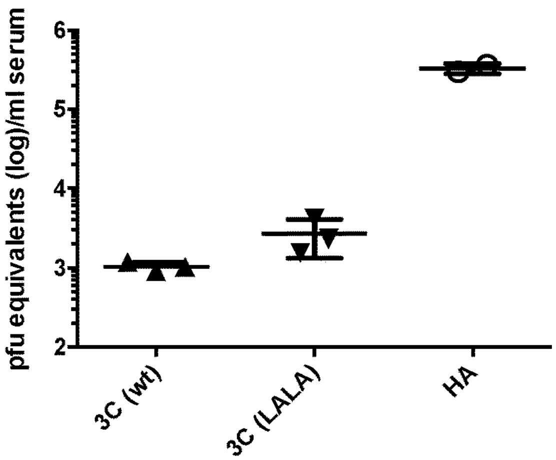

As shown in the in vitro analysis in FIG. 12, a modified antibody as described herein, as expected, abolishes the spike in the viral titre that is usually observed in antibody-dependent enhancement. When the antibody is tested in mice at low concentration, as shown in FIG. 13, the modification to the antibody as described herein only somewhat reduces virus titers in mice (as expected for the low amount of virus used) but importantly, does not cause an increase in viremia as observed for an antibody without Fc modification (FIG. 13A). Antibody with Fc modification marginally improves survival of mice (FIG. 13B) when compared to control unmodified antibody as described herein. When given as a prophylactic pre-infection treatment, the antibody as described herein significantly reduces virus titres (see FIG. 14 and FIG. 15). When given as a therapeutic treatment (i.e. antibody provided as post-infection treatment), the antibody as described herein could significantly reduce virus titer and improve mice survival (FIG. 16), even after a lethal challenge of dengue virus (FIG. 17B). Interestingly, the modified antibody, when compared to unmodified antibody, did not show change in efficacy in reducing virus titre in mice (FIG. 18, and FIG. 19). Thus, when taken together, the results demonstrate that the antibody as described herein, with or without the modification, could improve the survival of mice. At very low concentrations of unmodified antibody (i.e. below the minimum concentrations required to achieve neutralization of the virus) that causes ADE, Fc modification can abolish the enhancement effect in vitro and in mice.

Thus, in another aspect the present invention provides an isolated antibody, or antigen binding fragment thereof, as described herein, for use in a therapy. As the antibody as described herein appears to be able to neutralize dengue virus without causing unwanted antibody-dependent enhancement, in one example, the antibody, or antigen binding fragment thereof, as described herein, may be used for treating a subject with a dengue fever caused by at least one of the dengue virus serotypes, either during a first infection with the virus or during a re-infection with the virus.

In one example, the isolated antibody, or antigen binding fragment thereof, as described herein, may further comprise an agent including, but is not limited to, an antiviral agent, an immunoadhesion molecule, an imaging agent, a therapeutic agent, and the like.

In yet another aspect, there is provided a composition comprising the isolated antibody, or antigen binding fragment thereof, as described herein. In one example, the composition may further comprise a pharmaceutically acceptable excipient.

In yet another aspect there is provided a kit, comprising the isolated antibody as described herein. In one example, the kit may further comprise an agent, including but is not limited to, an antiviral agent, an immunoadhesion molecule, an imaging agent, a therapeutic agent, and the like. In one example, the kit may be used for treating a dengue virus infection in a subject.

In one example, the imaging agent may be selected from the group consisting of a radiolabel, an enzyme, a fluorescent label, a luminescent label, a bioluminescent label, a magnetic label and a biotin.

Figure 20:
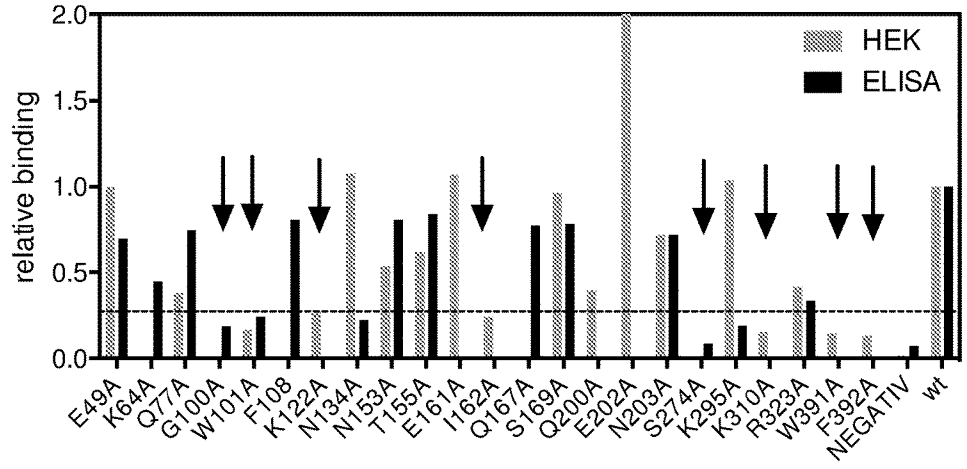
FIG. 20 shows the results into the investigation on the epitope recognized by 3C antibody.
Figure 20:
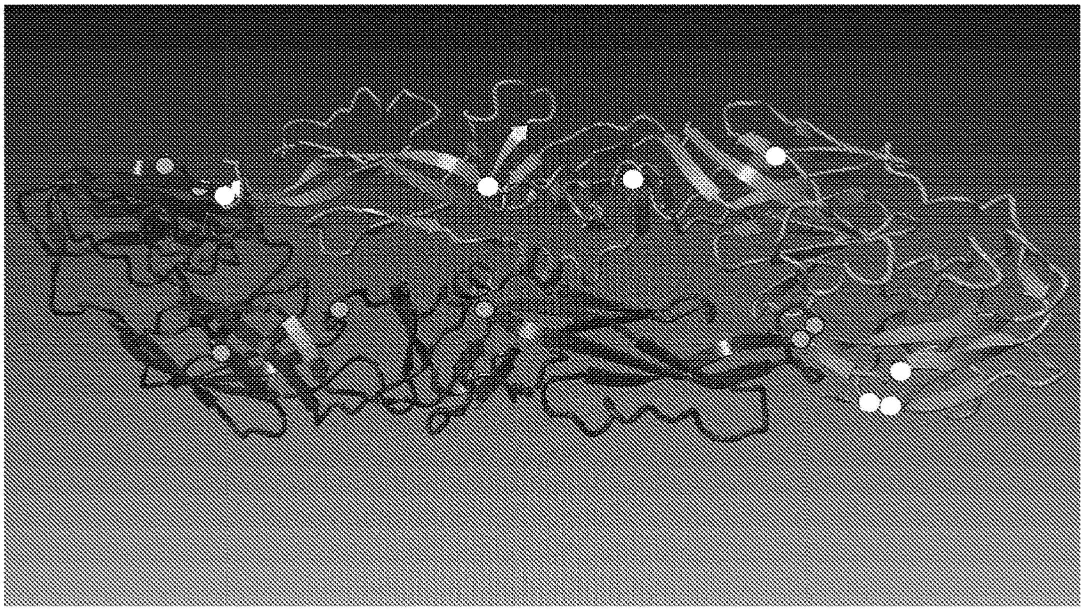

In one example, the antibody, or antigen binding fragment, as described herein may be specific to an epitope found in the dengue virus particle. In one example, the antibody, or antigen binding fragment, as described herein may be specific to, or recognize, or bind to, or capable of binding to, the epitope comprising at least one of the amino acids, including, but not limited to, K122, I162, and S274 (of DENV-2 that was used for epitope mapping as shown in FIG. 20). In one example, the antibody may recognize, bind to, or is capable of binding to, or is specific to, at least two, or at least three, or at least four, or at least five, or at least six, or at least seven, or all of the amino acids of a dengue virus peptide selected from the group consisting of K122, I162, and S274. In one example, the antibody, or antigen binding fragment thereof, wherein the epitope may further comprise at least one of the amino acids of a dengue virus glycoprotein selected from the group consisting of G100, W101, K310, W391, and F392, when the epitope comprises at least one, or at least two, all, of the amino acids of the dengue virus glycoprotein selected from the group consisting of K122, I162, and S274. In one example, the antibody, or antigen binding fragment thereof, wherein the epitope comprises at least two, or at least three, or at least four, or at least five, or at least six, or at least seven, or all, of the amino acids of a dengue virus glycoprotein selected from the group consisting of G100, W101, K122, I162, S274, K310, W391 and F392. In one example, the antibody, or antigen binding fragment thereof, is specific for an epitope comprising or consisting of G100, W101, K122, I162, S274, K310, W391 and F392 of a dengue virus glycoprotein. In one example, the antibody, or antigen binding fragment thereof, is specific for an epitope comprising or consisting of G100, W101, K122, I162, S274, K310, W391 and F392 of a dengue virus glycoprotein obtained from DENV2.

As used herein, the term "epitope" has its meaning as understood in the art. It will be appreciated by those of ordinary skill in the art that an epitope also known as antigenic determinant, is a molecular region of an antigen that is recognized by the immune system, specifically by antibodies, B cells, or T cells. It will be further appreciated that epitopes can be composed of sugars, lipids, or amino acids. The epitopes of protein antigens are divided into two categories, conformational epitopes and linear epitopes, based on their structure and interaction with the paratope (part of an antibody that recognizes the epitope). A conformational epitope is composed of discontinuous sections of the antigen's amino acid sequence and these epitopes interact with the paratope based on the 3-D surface features and shape or tertiary structure of the antigen. Linear epitopes interact with the paratope based on their primary structure and a linear epitope is formed by a continuous sequence of amino acids from the antigen. In one example, the amino acid identified to be the binding site of the antibody as described herein is described with its conventional abbreviation in the art. For example, G refers to glycine and the number following G refers to the relative position of the amino acid as compared to the start of the dengue virus protein monomer, which is part of a dimeric E protein complex that consists of two identical monomers as illustrated in a structure with PDB accession number 1OAN (RCSB PDB (Protein Data Bank) ID: 1OAN; DOI: 10.2210/pdbloan/pdb). As would be recognized in the art, W refers to tryptophan, K refers to lysine, I refers to isoleucine, S refers to serine, and F refers to phenylalanine. The epitope may also span across multiple E protein dimers as they are assembled on a virus particle.

As shown in FIG. 7, FIG. 8, FIG. 14, FIG. 15, and FIG. 18, the antibody, or antigen binding fragment, as described herein may be used in prophylactic treatment. Thus, in yet another aspect the present invention provides a passive vaccine. In one example, the passive vaccine against at least one of the dengue virus serotypes may comprise the isolated antibody as described herein or the composition as described herein or the kit as described herein. The term "vaccine", as used herein, refers to a composition intended to provide immune protection, for example to a disease causing agent. In one example, the vaccine may be administered before, during, and/or exposure to the disease-causing agent (for example dengue virus). As used herein, the term "passive vaccine" may be used interchangeably with "passive immunization", which is used to refer to immunization wherein antibodies are administered to a subject.

Figure 16:
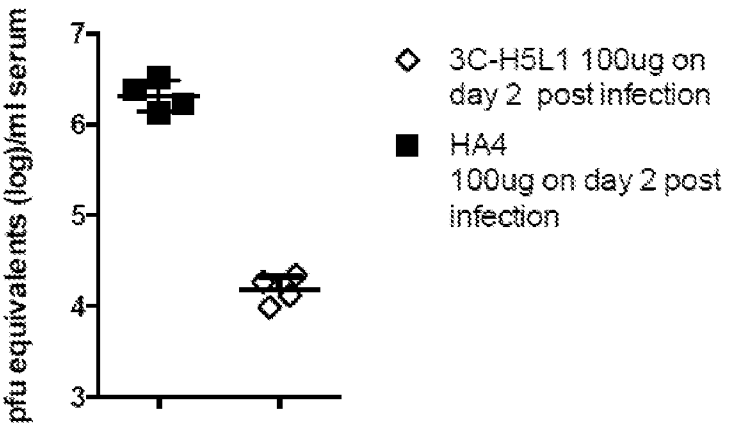
FIG. 16 shows results of analysis of post-infection treatment with 3C H5L1 antibody in mice. Mice were infected with $1\times10^7$ pfu DENV-2 strain D2Y98P intraperitoneally (i.p.). 48 h after infection 100 ug 3C-H5L1 or control Ab were transferred intravenously (i.v.) FIG. 16 A) shows a dot plot depicting the virus titre (or viremia) measured 24 h after antibody treatment (72 h after infection).
Figure 16:
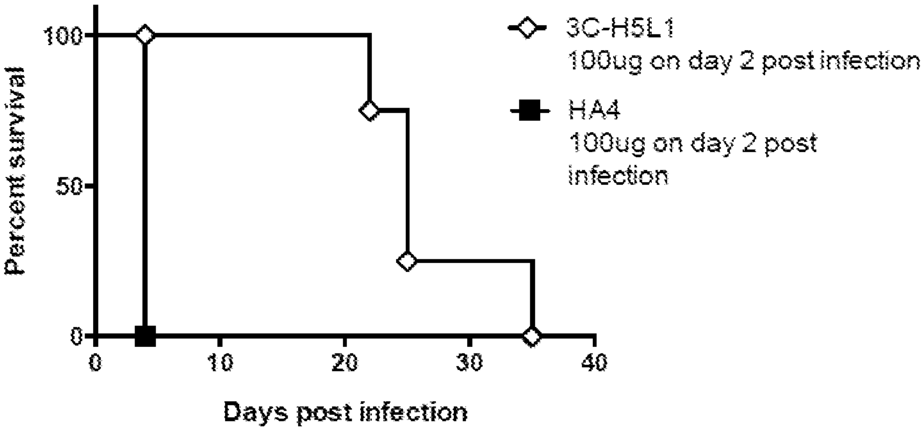
Figure 17:
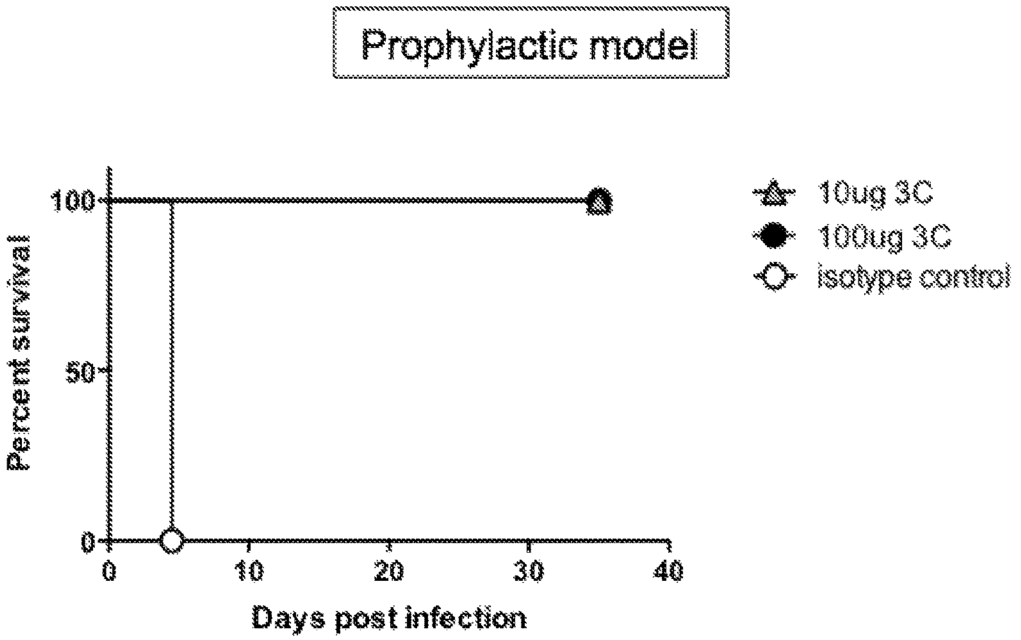
FIG. 17 shows the survival curve of mice receiving either pre-infection treatment (prophylactic model) or post-infection treatment (therapeutic model) after lethal challenge with DENV-2 D2Y98P. In A), AG129 mice were treated with either 10 μg or 100 μg of 3C antibody before lethal challenge with DENV-2 D2Y98P; and in B), IFNAR mice were infected first and treated two days later with 100 μg 3C antibody or control antibody.
Figure 17:
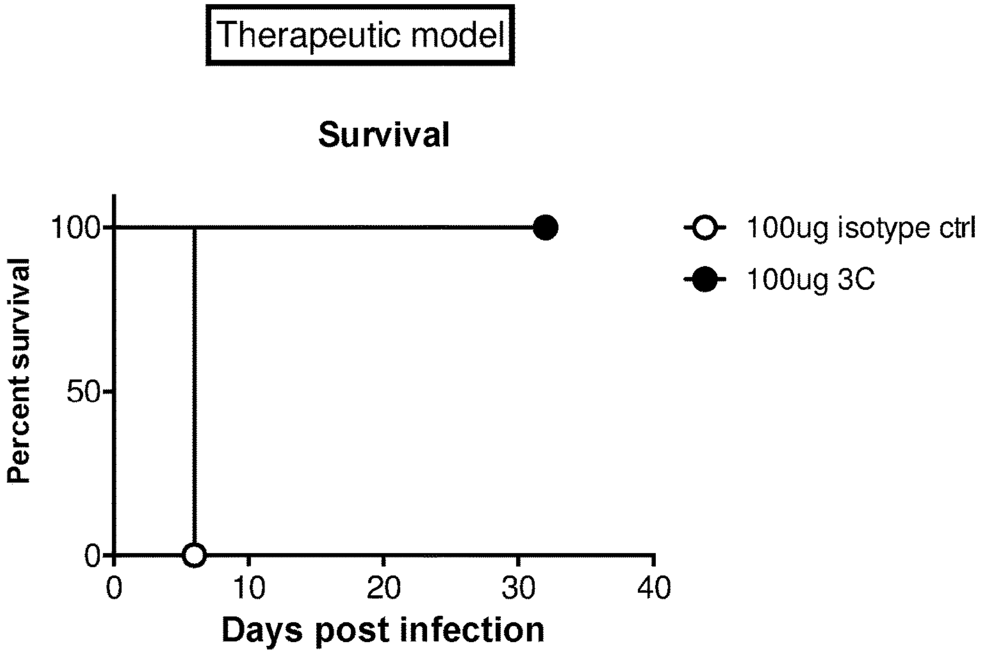

As shown in FIG. 16, FIG. 17B, and FIG. 19, the antibody, or antigen binding fragment, as described herein may be used in therapeutic treatment post-viral infection. Thus, in yet another aspect there is provided a method of treatment of a dengue virus infection in a subject. In one example, the method comprises administering to the subject an effective amount of the isolated antibody, or antigen binding fragment thereof, as described herein, or the composition as described herein, or the vaccine as described herein. In one example, the method further comprises administration of at least one additional therapy. In one example, the at least one additional therapy may be an antiviral therapy and/or anti-inflammatory agents. In yet another example, the additional therapy may be administered into the patient together or separately with the isolated antibody, or antigen binding fragment thereof.

As used herein throughout this disclosure, the term "subject" may be used interchangeably with the term "patient", which refers to any organism to which a provided composition, or antibody, or antigen binding fragment, as described herein may be administered. For example, the administration may be for experimental, diagnostic, prophylactic, cosmetic, and/or therapeutic purposes. Typical patients include animals (e.g., mammals such as mice, rats, rabbits, non-human primates, and/or humans). In one example, the subject may be a mammal. In one example, the mammal may be a human.

As used herein, the term "treatment" (also "treat" or "treating") refers to any administration of a substance (for example, the antibody, antigen binding fragment or composition as described herein) that partially or completely alleviates, ameliorates, relives, inhibits, delays onset of, reduces severity of, and/or reduces incidence of one or more symptoms, features, and/or causes of a particular disease, disorder, and/or condition (such as dengue fever). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some examples, treatment may be of a subject who has been diagnosed as suffering from the relevant disease, disorder, and/or condition. In some examples, treatment may be of a subject known to have one or more susceptibility factors that are statistically correlated with increased risk of development of the relevant disease, disorder, and/or condition.

In yet another aspect there is provided a use of the antibody, or antigen binding fragment thereof, as described herein or the composition as described herein, or the kit as described herein, or the vaccine as described herein, in the manufacture of a medicament for treating a dengue virus infection in a subject. In one example, the medicament may be administered with at least one additional therapy. In one example, the at least one additional therapy may be an antiviral therapy.

As used herein, throughout this disclosure, the term "antiviral therapy" refers to a class of medication or therapy used specifically for treating viral infections by inhibiting, deactivating, or destroying virus particles. In one example, an antiviral agent may be or comprise a compound of any chemical class (e.g., a small molecule, metal, nucleic acid, polypeptide, lipid and/or carbohydrate). In one example, an antiviral therapy or agent may be or may comprise an antibody or antibody mimic. In one example, an antiviral agent or therapy may be or may comprise a nucleic acid agent (e.g., an antisense oligonucleotide, a siRNA, a shRNA, etc) or mimic thereof. In one example, an antiviral therapy or agent may be or may comprise a naturally-occurring compound (e.g., small molecule). In one example, an antiviral therapy or agent may be or may have a chemical structure that is generated and/or modified by the hand of man.

In yet another example, the additional therapy may be administered into the patient together or separately with the isolated antibody, or antigen binding fragment thereof.

As shown in FIG. 4, the antibody as described herein may be used to bind to at least one dengue virus serotype. Accordingly, in yet another aspect there is provided a method for detecting at least one dengue virus serotype in a sample. In one example, the method comprises the steps of incubating the sample with at least one of the isolated antibody as described herein, or kit as described herein, and, detecting the antibody-dengue virus complex wherein the presence or absence of the complex indicates the presence or absence of dengue virus in the sample. The detail of methods of detecting a dengue virus serotype in a sample is known in the art and the person skilled in the art would be able to perform the methods without additional experimental burden.

In yet another aspect, there is provided an isolated nucleic acid molecule, including, but is not limited to, (a) a nucleic acid sequence encoding the isolated antibody, or antibody fragment thereof as described herein, (b) a nucleic acid sequence as shown in SEQ ID NOs: 1 and 2, (c) a nucleic acid complementary to any one of the sequences as described herein (i.e. (a) or (b)); (d) a nucleic acid sequence capable of hybridizing to (a), (b), or (c) under stringent conditions, and the like.

As used herein, the term "nucleic acid" in its broadest sense, refers to any compound and/or substance that is or can be incorporated into an oligonucleotide chain. In one example, a nucleic acid may be a compound and/or substance that is or can be incorporated into an oligonucleotide chain via a phosphodiester linkage. In one example, the term "nucleic acid" refers to individual nucleic acid residues (for example, nucleotides and/or nucleosides). In one example, the term "nucleic acid" refers to an oligonucleotide chain comprising individual nucleic acid residues. As used herein, the terms "oligonucleotide" and "polynucleotide" can be used interchangeably. In one example, "nucleic acid" encompasses RNA as well as single and/or double-stranded DNA and/or cDNA. Furthermore, the terms "nucleic acid", "DNA", "RNA", and/or similar terms include nucleic acid analogs, i.e., analogs having other than a phosphodiester backbone.

As used herein, the term "stringent conditions" refers to those conditions. The antibody variable regions in the heavy and light chain plasmid are amplified by PCR with primers binding in the non-variable part of the vector (5'TGTCCACTCCCAGGTCCAAG (SEQ ID NO: 13) and 5'TTTCCTTTATTAGCCAGAGG (SEQ ID NO: 14)) and the resulting PCR products are sequenced using Sanger sequencing to confirm the correct sequence as defined in SEQ ID NO:1 and SEQ ID NO:2.

In yet another aspect there is provided a vector comprising a nucleic acid sequence as described herein. As used herein, the term "vector" refers to a nucleic acid molecule capable of transporting another nucleic acid to which it is associated. In one example, vectors may be capable of extra-chromosomal replication and/or expression of nucleic acids to which they are linked in a host cell such as a eukaryotic and/or prokaryotic cell. Vectors may be capable of directing the expression of operatively linked genes are referred to herein as "expression vectors".

In yet another aspect, there is provided a host transformed with the vector as described herein. In one example, the host is a cell. In one example, the host may be a cell, which may include, but is not limited to, a human, bacterial, animal, fungal, amphibian, plant cell, and the like, which are known to be capable of producing antibodies, or antigen binding fragment thereof, as described herein. In one example, the cell is a cell line.

In one example, the cell line may be generated from cells known in the art, for example, a human embryonic kidney 293 cells (HEK293), CHO, 293, 293e, plant cells, insect cells and the like.

Those skilled in the art will recognize that the generation of antibody or antigen binding fragment thereof may be performed in animal. Thus, in one example, the host may be a non-human transgenic animal.

In another aspect, there is provided a process of manufacturing an antibody, or antigen binding fragment as described herein, comprising the step of obtaining the antibody from the host as described herein.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Materials

The sequence for Ab 3C H5L1 was isolated from plasmablasts from a patient with acute dengue infection as described in Xu and Hadinoto et al, J. Immunol, 2012, Dec. 15; 189 (12): 5877-85. Doi: 10.4049/jimmunol.1201688 (the content of which is incorporated herein by reference). Single $CD19^{+}CD20^{-}CD38^{high}CD27^{high}$ plasmablasts were sorted with a FACSAria into 96 well plates containing Tris buffer and RNAse inhibitor, and frozen immediately. After thawing, mRNA of human IgG heavy and kappa light chain were amplified individually from single B cells by RT-PCR according to the protocol published by (Smith et al. 2009. Rapid generation of fully human monoclonal antibodies specific to a vaccinating antigen. Nat Protoc 4:372-384, the content of which is incorporated herewith by reference). The variable regions of heavy and light chain were cloned into IgG1 expression plasmids (licensed from the National Research Council Biotechnology Research Institute, Canada). Heavy and light chain plasmids were co-transfected into HEK293-6E cells using 293fectin for the transient expression of antibodies. The secreted IgG1 antibody was purified from the culture supernatant using Protein A beads.

Methods

The antibody was expressed recombinantly in HEK293e cells and was tested in ELISA, Neutralisation assay, immunofluorescence and in vivo in mice.

Viruses

All viruses used were produced in C6/36 mosquito cells (ATCC). The following patient isolate dengue virus strains were used: DENV1-05K2916; also referred to as "167" (EU081234), DENV-1-08K3126 (isolated by Environmental Health Institute, Singapore), DENV2-TSV01 (AY037116.1), DENV-2 D2Y98P (JF327392.1), DENV3-VN32/96 (EU482459), DENV4-2641Y08 (isolated by Environmental Health Institute, Singapore), and DENV-4 TVP360 (WHO reference strain).

ELISA (Enzyme Linked Immunosorbent Assay)

For DENV-specific ELISA (FIG. 1), MaxiSorp plates (Nunc) were coated with PEG-precipitated, heat-inactivated DENV serotypes 1-4. Plates were blocked with PBS, 0.05% Tween 20 (PBST) and 3% skimmed milk. Supernatants from Ab-expressing HEK cells were incubated on virus-coated plates for 1 h at RT before washing with PBST and detection of virus-binding antibodies with a secondary anti-human IgG-HRP (Sigma). Absolute concentrations of IgG were determined by IgG-specific ELISA, including a IgG standard of known concentration. In FIG. 2, ELISA plates were coated with 4G2 antibody (binding to E protein of all four serotypes, from ATCC) and blocked with Casein. Plates were then incubated with live virus particles and washed before the addition of antibodies. E protein-specific antibodies were measured on plates coated with 150 ng/well E protein of DENV-1, -2, -3 or -4, which were produced in S2 cells as described in (Umashankar et al 2008. Differential cholesterol binding by class II fusion proteins determines membrane fusion properties. J Virol 82:9245-9253, the content of which is incorporated herewith by reference). 293HEK cell supernatants or purified antibodies were used for screening. Pooled serum from several dengue-immune healthy donors was used as a positive control. 3,3,5,5-tetramethylbenzidine HRP substrate solution (TMB, Sigma) was used as substrate for all ELISAs. An OD value 2-fold higher than the background was defined as a positive signal.

Plaque Reduction Neutralization Assay

BHK-21 cells ($1\times10^5$/well) were seeded in 24-well plates and cultured overnight at 37° C. Antibody 3C diluted to different concentrations (30 μg-0.3 μg/ml) in serum-free medium was mixed with an equal volume of DENV and incubated at room temperature for 2 h. Virus-antibody mixtures (100 μl) were transferred to the 24-well plates and incubated for 1 hr at 37° C. before adding an equal volume of RPMI containing 10% FCS and 0.8% methylcellulose.

After 4.5 days, cells were fixed with 3.7% formalin. The overlay was discarded and cells were stained with crystal violet containing 0.8% PFA. Plaques were counted by eye and PRNT50 values were calculated using the three-parameter non-linear curve fit in Graphpad Prism software.

Immunohistochemistry

BHK-21 cells were seeded in 96-well plates and infected with DENV-1, DENV-2, DENV-3 and DENV-4 at MOI 1 for 1 hr at 37° C. After removing the virus RPMI containing 5% FCS, 1% Pen/strep was added to the cells and cells were incubated at 37° C. 48 h post-infection cells were fixed with 4% PFA for 20 mins at room temperature (RT). All washes were performed with phosphate-buffered saline (PBS) for 10 mins. Cells were permeabilize with 1×PBS+0.05% Triton X-100 for 15 mins at RT, followed by blocking (1×PBS+1% BSA) for 1 hr at RT. Cells were incubated with antibody 3C (1 μg/ml) for 1 hr at RT, washed and incubated with anti-human IgG-AlexaFluor488 for 1 hr at RT. After two washes, Hoechst 33342 was added for 5 min at RT. Antibody binding was visualized using an Olympus confocal microscope with AlexaFluor488-specific barrier and excitation filter.

Mechanism of Neutralization: Pre- and Post-Attachment Neutralization Assay

A pre- and post-attachment neutralization assay was performed to assess whether 3C antibody would still be able to neutralize once virus particle have already bound to the target cell. The assay was done with U937-DC-SIGN cells. The protocol was adapted from Matthew R. Vogt, et al. Journal of Virology 2009:6494-6507 (the contents of which are incorporated herewith by reference) and Crill et al. Journal of Virology 2001: 7769-7773 (the contents of which are incorporated herewith by reference). For the pre-attachment neutralization assay cells were pre-chilled. A constant amount of virus was mixed with antibody at 10-0.001 μg/ml final concentration and incubated at 4° C. for 1 hr. Antibody-virus-mixtures were added to the pre-chilled cells and incubated at 4° C. for 1 hr. Cells were washed three times and then incubated at 37° C. for 48 h. Cells were washed, fixed, stained intracellularly with antibodies binding to E protein and NS1 protein and analyzed by flow cytometry. The percentage of infected cells per Ab concentration was plotted for the calculation of the EC50, using Prism (Graphpad) software. For the post-attachment neutralization assay cells were pre-chilled. Virus was added (same amount as above) and incubated for 1 hr at 4° C. Cells were washed three times. Antibody was added at a final concentration of 10-0.001 μg/ml and incubated for 1 hr at 4° C. Cells were washed three times and then incubated at 37° C. for 48 hr. Staining of cell was performed as for the pre-attachment assay.

As illustrated in FIG. 5, neutralizing effect was observed in both pre- and post-attachment of the virus to cells. However, there is a trend of more efficient neutralization in pre-attachment experiment.

Mechanism of Neutralization: Fusion Inhibition

An essential part of a successful infection is the fusion of the dengue virus particle with the host cell. Once the virus fuses with the host membrane the viral RNA can be released into the cytoplasm and can be translated, initiating the replication of the virus. After the virus is taken up by the cell the fusion event occurs in the endosome, triggered by the low pH in this cell compartment. It is known that some dengue antibodies are able to block this fusion event. The method for testing this in vitro is to use C6/36 cells, which have a cell membrane composition like human endosomes. Upon decreasing the pH in vitro the infected cells fuse. These fusions are permeable and nuclei are stained with propidium iodide (PI). The method is described in detail by Rajamanonmani et al, Journal of General Virology 2009 (90) 799-809 (the contents of which are incorporated herewith by reference). In brief, 500,000 C6/36 cells per well were mixed with DENV-2 TSV01 MOI 0.01 and incubated in a 96 well plate for 72 hr at 28° C. Antibody at different concentrations were then added to the cells and incubated for 1 hr at 28° C. 0.5M MES buffer pH 5 (final concentration 0.0125M) was added to induce sycytia formation (1 hr at 37° C.). Medium was removed and a 0.025 mg/ml propidium iodide (PI) in RPMI solution was added to the cells and incubated at 28° C. for 30 min. Cells were then immediately imaged using a confocal microscope.

Antibody Dependent Enhancement (ADE) Assay

Equal volumes of a constant amount of virus and a decreasing amount of antibody 3C (starting from 30 μg/ml) were incubated for 1 hr at 37° C. These virus-antibody mixtures were then transferred to K562 cells pre-aliquoted in round bottom 96 well plates and incubated for 1 hr at 37° C. Cells were washed twice with PBS and incubated in RPMI medium with FCS for 72 hr. Virus in the supernatants of infected K562 cells was determined using a BHK-21 cell based plaque assay and crystal violet staining as described for the plaque reduction neutralization assay.

Mouse Model

Interferon alpha/beta/gamma-Receptor knock out mice on a Sv129 background (AG129) mice (U&K Universal, UK) and Interferon alpha/beta-Receptor knock out mice on a C57BL-6 background (IFNAR) mice (originally from Prof. Michel Aguet, EPFL, Switzerland) were housed under SPF conditions at the Biological Resource Center (BRC), Singapore. The animal experiments were conducted according to the rules and guidelines of the Agri-Food and Veterinary Authority (AVA) and the National Advisory Committee for Laboratory Animal Research (NACLAR), Singapore. The experiments were reviewed and approved by the Institutional review board of Biological Resource Center, Singapore.

The following virus strains were used for infection: DENV-1 08 K3126, DENV-2 TSV01 or D2Y98P, DENV-3 VN-32/96, DENV-4 TVP360.

In Vivo Assays—Pre-Infection Treatment (Prophylactic)

Ab in 100 μl PBS was injected intravenously via the retro-orbital sinus. Mice were infected intraperitoneally 24 hr with DENV in RPMI medium. Three days after infection mice were bled from the retro-orbital sinus into tubes containing 20 μl sodiumcitrate as an anti-coagulant. Blood tubes were centrifuged for 5 min at 1000 g and plasma was collected and frozen for later analysis.

In Vivo Assays—Post-Infection Treatment (Therapeutic)

Mice were infected intraperitoneally with DENV in RPMI medium. 48 hr after infection Ab 3C H5L1 was injected intravenously via the retro-orbital sinus. 24 hr later (day 3 after infection) blood was collected via the retro-orbital sinus into tubes containing 20 μl sodiumcitrate as an anti-coagulant. Blood tubes were centrifuged for 5 min at 1000 g and plasma was collected and frozen for later analysis.

Figure 14:
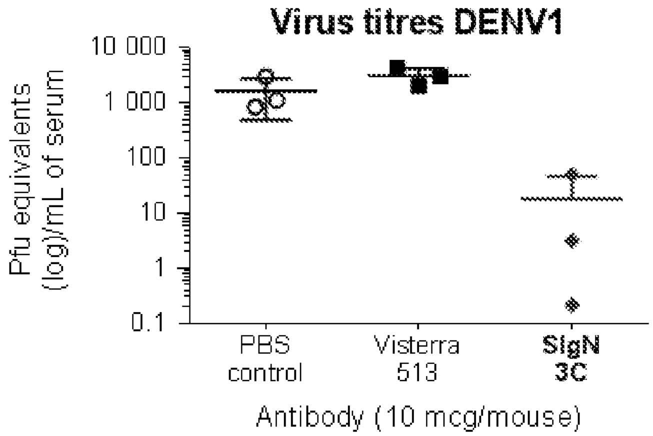
FIG. 14 shows dot plot graphs depicting the virus titers in IFNAR mice with or without antibody pre-treatment. 10 μg antibody was injected per mouse. $5\times10^5$ pfu DENV-1 strain 08K3126 and $10^7$ pfu DENV-2 strain D2Y98P were used for the challenge. Mice were treated with either PBS control, modified antibody 513 from Visterra (i.e. with LALA mutation), or modified 3C H5L1 antibody (i.e. with LALA mutation).
Figure 14:
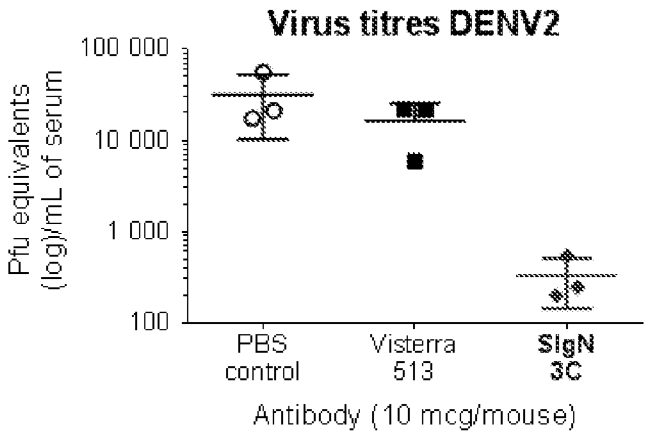
Figure 15:
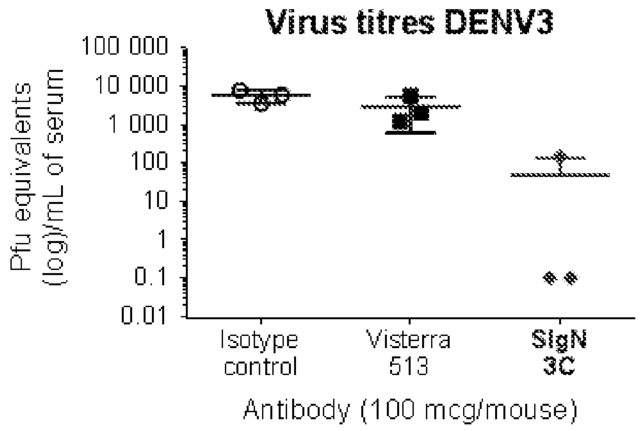
FIG. 15 shows dot plot graphs depicting the virus titers in AG129 mice with or without antibody pre-treatment. 100 ug antibody was injected per mouse. $1.5\times10^6$ pfu DENV-3 strain VN32/96 and $10^8$ pfu DENV-4 strain TVP360 were used for the challenge. Mice were treated with either PBS control, modified antibody 513 from Visterra (i.e. with LALA mutation), or modified 3C H5L1 antibody (i.e. with LALA mutation).
Figure 15:
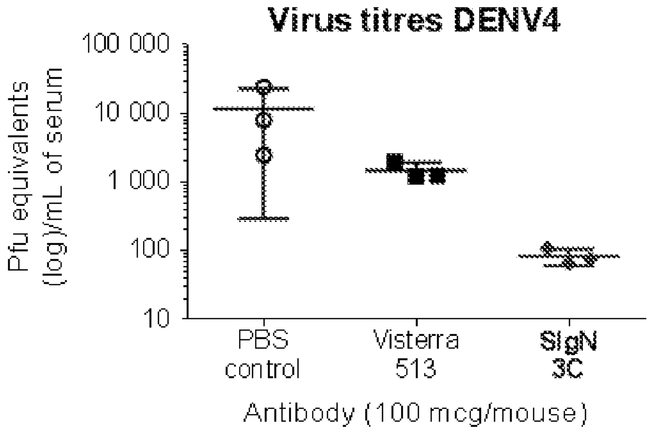

Efficacy Against all Four DENV Serotypes in the Prophylactic Model and Comparison of Ab 3C with a Published Therapeutic Dengue Antibody In FIG. 14 and FIG. 15, AG129 mice or IFNAR mice were used to assess prophylactic protection of the antibodies against DENV-1, -2, -3 and -4. Viremia was tested at day 3 or day 4 after infection. Efficacy in AG129 and IFNAR mice is very similar (compare FIGS. 19A and B). It appears that the IFN-gamma receptor has no impact on efficacy, at least early after infection. Mice were treated with antibodies as described in "In vivo assays—pre-infection treatment (prophylactic)". In the same experiment efficacy of antibody 3C was compared with efficacy of antibody 513 from Visterra (patent describing the sequence is published). Both antibody batches were produced at the same time by Chugai, and both antibodies contain a LALA mutation in the Fc part. Mice were treated with antibodies as described in "In vivo assays—pre-infection treatment (prophylactic)". 10 μg per antibody was used for DENV-1 and DENV-2, and 100 ug per antibody was used for DENV-3 and DENV-4. The results show that 3C decrease viremia more efficiently than Ab 513 for all four DENV serotypes.

Efficacy Against DENV-2 in the Therapeutic Model

DENV-2 D2Y98P causes death and therefore the DENV-2 model was used to assess the protective capacity of Ab 3C.

Epitope of 3C

A number of full length E protein mutants of DENV-2 were transiently expressed in HEK293 cells and the binding of 3C to these transfected HEK cells was tested by flow cytometry.

In addition, the soluble part of the E protein was also expressed in S2 cells. Various mutants and the wildtype form of DENV-2 (strain TSV01) were expressed, purified and used in ELISA. The E proteins contain a V5 tag and the plates were coated with anti-V5 antibody, followed by adding the individual E proteins. This sandwich approach increases the binding of 3C compared to an ELISA where the E protein is coated to the plate directly, possibly due to multimerization of the E protein.

Mutations were introduced using QuikChange site directed mutagenesis kit (Agilent Genomics). HEK293 cells were seeded at 100,000 cells/well in a 24 well plate and incubated over night. Cells were then transfected with 1 μg pcDNA3.1 containing the prM and E protein of DENV-2 TSV01 using 293 transfectin according to manufacturers protocol. 72 hours post infection the cells were harvested and analysed by flow cytometry: transfected HEK cells were incubated with 3C antibody, followed by incubation with anti-human IgG-FITC. To test for expression of E protein mutants antibody 3H5 specific for DENV-2 EDIII (from ATCC) was used, followed by incubation with anti-mouse IgG-FITC. The following formula was used to calculate relative binding: relative binding of 3C for E protein mutant x=[(% FITC-positive cells stained with 3C/anti-human IgG for mutant x)/(% FITC-positive cells stained with 3H5/anti-mouse IgG for mutant x)]/[(% FITC-positive cells stained with 3C/anti-human IgG for wt E protein)/(% FITC-positive cells stained with 3H5/anti-mouse IgG for wildtype E protein)].

For ELISA, a number of E protein mutants (the soluble part of E protein) were expressed in S2 cells as described in the section "ELISA". Mutations were introduced using QuikChange site directed mutagenesis kit (Agilent Genomics). The E protein constructs also contain a V5 tag. E protein mutants were purified using chelating sepharose beads. Nunc immune-assay ELISA plates were coated with mouse anti-V5 tag antibody. After blocking with 3% mild in PBST, E protein mutants at 5 ug/ml were added to the wells for 2 h. After washing, antibody 3C was added to all E protein mutants in duplicate and incubated for 1 h at RT. 3C was detected with anti-human IgG-HRP. TMB substrate was used to develop a color reaction. As a positive control a mixture of three human dengue antibodies with different epitopes was used. Binding of this positive control was similar for all E protein mutants and therefore the values for 3C binding to each mutant was only divided by the value for 3C binding to the wildtype E protein.

A number of full length E protein mutants of DENV-2 were transiently expressed in HEK293 cells and the binding of 3C to these transfected HEK cells was tested by flow cytometry. In addition, the soluble part of the E protein was also expressed in S2 cells. Various mutants and the wildtype form of DENV-2 (strain TSV01) were expressed, purified and used in ELISA. The E proteins contain a V5 tag and the plates were coated with anti-V5 antibody, followed by adding the individual E proteins. This sandwich approach increases the binding of 3C compared to an ELISA where the E protein is coated to the plate directly, possibly due to multimerization of the E protein.

In FIG. 20, relative binding of 3C to the E protein mutants indicated on the x-axis. The binding to wildtype protein (wt E protein) was used to normalize binding to mutants. The binding observed using the HEK cell approach is indicated in grey bars whereas the binding observed in ELISA is indicated in black bars. For K64A, G100A, F108A, Q167A, and S274A, only ELISA was done. For K122A, I162A, Q200A, E202A, K310A, W391A, and F392A, only the HEK cell expression assay was done. The dotted line indicates the 75% reduction in binding compared to wt E protein that was arbitrarily chosen as a cut-off for loss of binding due to the mutation.

TABLE 1

Relative binding of 3C H5L1 to E protein mutants in the HEK and/or the ELISA assay. Amino acid substitutions in the E protein that result in more than 75% loss of binding are highlighted in bold letters. These highlighted amino acids define the epitope of 3C H5L1 in the assays used here.

| | HEK | ELISA |
|---|---|---|
| E49A | 0.9957073 | 0.6953955 |
| K64A | | 0.4441286 |
| Q77A | 0.3799409 | 0.7472253 |
| **G100A** | | 0.1862654 |
| **W101A** | 0.1646154 | 0.2416909 |
| F108 | | 0.8061085 |
| **K122A** | 0.2701714 | |
| N134A | 1.076023 | 0.2214801 |
| N153A | 0.5353212 | 0.805963 |
| T155A | 0.6206209 | 0.8386407 |
| E161A | 1.069562 | |
| **I162A** | 0.2423869 | |
| Q167A | | 0.7740121 |
| S169A | 0.9633535 | 0.784286 |
| Q200A | 0.394081 | |
| E202A | 2.024244 | |
| N203A | 0.7187698 | 0.7201147 |
| **S274A** | | 0.08588301 |
| K295A | 1.036517 | 0.189356 |
| **K310A** | 0.150000 | |
| R323A | 0.4162633 | 0.3338105 |
| **W391A** | 0.144225 | |
| **F392A** | 0.1325641 | |
| NEGATIV | 0.01564103 | 0.070000 |
| wt | 1.000000 | 1.000000 |

SUMMARY

3C H5L1 antibody binds to and neutralizes DENV-2 and, to a lesser extent, but still very potently (with EC50 in the mM to nM range), DENV-1, 3, 4 in vitro. 3C H5L1 antibody does bind to whole virus particles and not efficiently to recombinant E protein. 3C H5L1 antibody has a remarkable in vivo efficacy against all four DENV serotypes in vivo and protects against death from a lethal DENV-2 strain. The observed antibody-dependent enhancement (i.e. ADE) with low amounts of 3C H5L1 can be completely abolished by introducing a modification (such as a LALA mutation) in the Fc part of 3C H5L1 without compromising in vivo efficacy. The observed efficacy against four serotypes and protection against lethal DENV-2 is unmet by other known antibodies against dengue virus (i.e. DENV). Whilst very potent neutralizing antibodies known in the art are usually specific for one serotype, the antibody as described herein has been shown to possess neutralizing capability towards multiple DENV serotypes. In fact, in vivo, the antibodies as described herein appear to be potent towards all four DENV serotypes.

What is claimed is:

1. An isolated antibody, or antigen binding fragment thereof, comprising:

a heavy chain amino acid sequence comprising all of the CDRs of (a) a CDRH1 as shown in SEQ ID NO: 3, (b) a CDRH2 as shown in SEQ ID NO: 4, (c) a CDRH3 as shown in SEQ ID NO: 5, and a light chain amino acid sequence comprising all of the CDRs of (a) a CDRL1 as shown in SEQ ID NO: 6, (b) a CDRL2 as shown in SEQ ID NO: 7, (c) a CDRL3 as shown in SEQ ID NO: 8, wherein the antibody or antigen binding fragment thereof recognizes a whole dengue virus particle.

2. The antibody, or antigen binding fragment thereof according to claim 1, wherein said antibody is specific for an epitope comprising at least one of the amino acids of a dengue virus glycoprotein selected from the group consisting K122, I162, and S274.

3. The antibody, or antigen binding fragment thereof, of claim 2, wherein the epitope further comprises at least one of the amino acids of a dengue virus glycoprotein selected from the group consisting of G100, W101, K310, W391, and F392, when the epitope comprises at least one of the amino acids of the dengue virus glycoprotein selected from the group consisting K122, I162, and S274; or wherein the epitope comprises at least three of the amino acids of a dengue virus glycoprotein selected from the group consisting of G100, W101, K122, I162, S274, K310, W391 and F392.

4. The antibody, or antigen binding fragment thereof according to claim 1, wherein the antibody is capable of binding to a whole dengue virus particle better than binding to a dengue virus surface glycoprotein.

5. The antibody, or antigen binding fragment thereof according to claim 2, wherein the glycoprotein is an E protein.

6. The antibody, or antigen binding fragment thereof according to claim 1, wherein the dengue virus particle is at least one dengue virus selected from the group consisting of DENV serotype 1 (DENV-1), DENV serotype 2 (DENV-2), DENV serotype 3 (DENV-3), and DENV serotype 4 (DENV-4).

7. The antibody, or antigen binding fragment thereof according to claim 1, wherein the antibody comprises a heavy chain variable region encoded by a nucleotide sequence having at least 90% sequence identity to SEQ ID NO: 1.

8. The isolated antibody, or antigen binding fragment thereof according to claim 1, wherein the antibody comprises a heavy chain variable region encoded by the nucleotide sequence SEQ ID NO: 1.

9. The isolated antibody, or antigen binding fragment thereof according to claim 1, wherein the antibody comprises a light chain variable region encoded by the nucleotide sequence having at least 90% sequence identity to SEQ ID NO: 2.

10. The isolated antibody, or antigen binding fragment thereof according to claim 1, wherein the antibody comprises a light chain variable region encoded by the nucleotide sequence SEQ ID NO: 2.

11. The isolated antibody, or antigen binding fragment thereof according to claim 1, wherein the antibody, or antigen binding fragment thereof, comprises a heavy chain variable region comprising the amino acid sequence of SEQ ID NO: 9, or an amino acid sequence having a sequence identity of at least 90% thereto.

12. The isolated antibody, or antigen binding fragment thereof according to claim 1, wherein the antibody, or antigen binding fragment thereof, comprises of a light chain variable region comprising the amino acid sequence of SEQ ID NO: 10, or an amino acid sequence having a sequence identity of at least 90% thereto.

13. The isolated antibody, or antigen binding fragment thereof according to claim 1, wherein said antibody is a monoclonal antibody.

14. The isolated antibody, or antigen binding fragment thereof according to claim 1, wherein the antibody is a modified IgG1 antibody, a modified IgG2 antibody, a modified IgG3 antibody, or a modified IgG4 antibody.

15. A method of treatment of a dengue virus infection in a subject, comprising administering to the subject an effective amount of the isolated antibody, or antigen binding fragment thereof, according to claim 1.

16. An isolated nucleic acid molecule comprising:

a nucleic acid sequence encoding an isolated antibody, or antibody fragment thereof, according to claim 1, or a nucleic acid sequence complementary thereto.

* * * * *